(12) United States Patent
Kim et al.

(10) Patent No.: US 12,116,360 B2
(45) Date of Patent: Oct. 15, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Soo Yeon Kim, Cheonan-si (KR); Hye Jeong Kim, Cheonan-si (KR); Hyung Dong Lee, Cheonan-si (KR); Jung Geun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/400,275

(22) Filed: Dec. 29, 2023

(65) Prior Publication Data

US 2024/0190852 A1 Jun. 13, 2024

Related U.S. Application Data

(63) Continuation-in-part of application No. 18/568,709, filed as application No. PCT/KR2022/009846 on Jul. 7, 2022.

(30) Foreign Application Priority Data

Jul. 21, 2021 (KR) .................. 10-2021-0095920
Aug. 19, 2021 (KR) .................. 10-2021-0109156
Aug. 19, 2021 (KR) .................. 10-2021-0111784

(51) Int. Cl.
*C07D 407/12* (2006.01)
*C07D 307/91* (2006.01)
(Continued)

(52) U.S. Cl.
CPC ......... *C07D 407/12* (2013.01); *C07D 307/91* (2013.01); *C07D 333/76* (2013.01);
(Continued)

(58) Field of Classification Search
CPC .. C07D 407/12; C07D 409/12; H10K 85/633; H10K 85/636
See application file for complete search history.

(56) References Cited

U.S. PATENT DOCUMENTS

2018/0093962 A1* 4/2018 Choi .................... C07D 409/12
2023/0040837 A1* 2/2023 Kim .................... C07D 409/12

FOREIGN PATENT DOCUMENTS

CN 108134009 A * 6/2018 .......... C07D 307/91
CN 111196822 A 5/2020
(Continued)

OTHER PUBLICATIONS

Machine-generated English-language translation of KR-20170116843-A.*
(Continued)

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound represented by Formula (1) capable of improving the light-emitting efficiency, stability, and lifespan of an element; a composition comprising the same; an organic electronic element using same; and an electronic device thereof.

13 Claims, 2 Drawing Sheets

(51) Int. Cl.
*C07D 333/76* (2006.01)
*C07D 409/12* (2006.01)
*H10K 50/11* (2023.01)
*H10K 50/15* (2023.01)
*H10K 50/16* (2023.01)
*H10K 50/17* (2023.01)
*H10K 85/60* (2023.01)

(52) U.S. Cl.
CPC ........... *C07D 409/12* (2013.01); *H10K 50/11* (2023.02); *H10K 50/15* (2023.02); *H10K 50/16* (2023.02); *H10K 50/171* (2023.02); *H10K 85/6574* (2023.02); *H10K 85/6576* (2023.02)

(56) References Cited

FOREIGN PATENT DOCUMENTS

| | | | | | |
|---|---|---|---|---|---|
| CN | 111635324 | A | * | 9/2020 | ........... C07C 211/61 |
| CN | 112266371 | A | | 1/2021 | |
| CN | 112480011 | A | * | 3/2021 | ........... C07D 235/18 |
| CN | 112759582 | A | * | 5/2021 | ........... C07D 209/86 |
| EP | 3444241 | A1 | * | 2/2019 | ........... C07C 211/61 |
| KR | 20170116843 | A | * | 10/2017 | ........... C07D 471/06 |
| KR | 20180000323 | A | * | 1/2018 | ........... C07D 487/04 |
| KR | 10-2018-0041607 | A | | 4/2018 | |
| KR | 10-2018-0118748 | A | | 10/2018 | |
| KR | 10-2076958 | B1 | | 2/2020 | |
| WO | WO-2019022458 | A1 | * | 1/2019 | ........... C07D 213/16 |
| WO | WO-2020220942 | A1 | * | 11/2020 | ........... C07C 211/58 |
| WO | WO-2021060723 | A1 | * | 4/2021 | |
| WO | WO-2021101247 | A1 | * | 5/2021 | ........... C07D 405/12 |
| WO | 2021/141356 | A1 | | 7/2021 | |
| WO | WO-2021136006 | A1 | * | 7/2021 | ........... C07D 209/86 |

OTHER PUBLICATIONS

Machine-generated English-language translation of CN-112759582-A.*

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

CROSS REFERENCE OF RELATED APPLICATIONS

This application is a continuation-in-part of U.S. patent application Ser. No. 18/568,709 filed on Dec. 8, 2023, which was a 371 of PCT/KR2022/009846 filed on Jul. 7, 2022, which claims the benefit of priority from Korean Patent Application No. 10-2021-0111784 filed on Aug. 19, 2021, Korean Patent Application No. 10-2021-0109156 filed on Aug. 19, 2021 and Korean Patent Application No. 10-2021-0095920 filed on Jul. 21, 2021, the contents of each of which are incorporated herein by reference in its entirety.

BACKGROUND

[Technical Field]

The present invention relates to a compound for an organic electronic element, an organic electronic element using the same, and an electronic device thereof.

[Background Art]

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

The most problematic issues with organic electroluminescent devices are lifespan and efficiency, and as displays become larger in area, these efficiency and lifespan issues must be resolved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to each of the emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value, therefore the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic element are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against Joule heating generated when the device is driven, while delaying penetration of the metal oxide from the anode electrode (ITO), which is one of the causes of shortening the lifespan of the organic electronic element, into the organic layer. The low glass transition temperature of the hole transport layer material has a characteristic that when the device is driven, the uniformity of the surface of the thin film is lowered, which has been reported to have a great influence on the lifespan of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required.

Therefore, the development of new materials continues to be required, and in particular, the development of materials for the emitting-auxiliary layer is urgently required.

DETAILED DESCRIPTION OF THE INVENTION

[Summary]

In order to solve the problems of the background art described above, the present invention has revealed a compound having a novel structure, and that when the compound is applied to an organic electronic element, the luminous efficiency, stability and lifespan of the element are greatly improved.

Accordingly, it is an object of the present invention to provide a novel compound, an organic electronic element using the same, and an electronic device thereof.

Technical Solution

The present invention provides a compound represented by Formula (1).

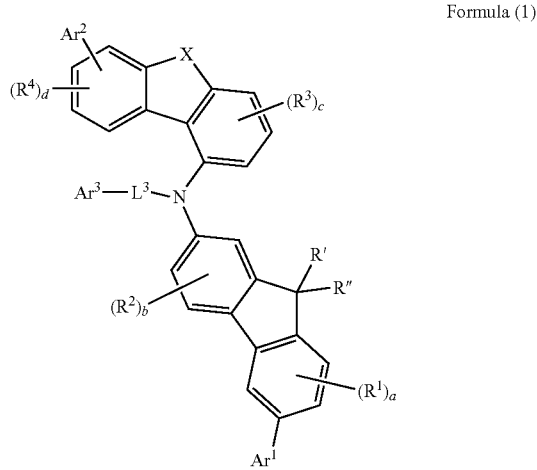

Formula (1)

In another aspect, the present invention provides an organic electronic element comprising a compound represented by Formula (1) and an electronic device thereof.

[Effects of the Invention]

By using the compound according to the present invention, it is possible to achieve a high luminous efficiency, a low driving voltage, and a high heat resistance of the element, and can greatly improve the color purity and lifespan of the element.

Figure 1:
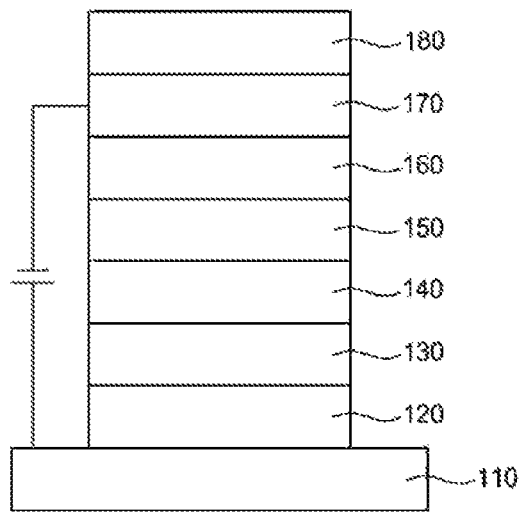
FIG. 1 to FIG. 3 illustrate an example of an organic electronic element according to the present invention.

| 100, 200, 300: organic electronic element | 110: the first electrode |
| --- | --- |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected","coupled" or "connected" between each component.

As used in the specification and the accompanying claims, unless otherwise stated, the following is the meaning of the term as follows.

Unless otherwise stated, the term "halo" or "halogen", as used herein, includes fluorine(F), bromine(Br), chlorine(Cl), or iodine(I).

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including SO₂ instead of carbon consisting of cycle. For example, "heterocyclic group" includes compound below.

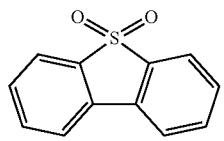 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

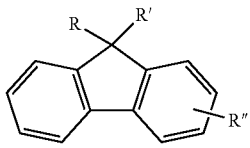

The term "spiro compound", as used herein, has a 'spiro union', and a spiro union means a connection in which two rings share only one atom. At this time, atoms shared in the two rings are called 'spiro atoms', and these compounds are called 'monospiro', 'di-spiro' and 'tri-spiro', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include one or more heteroatoms, but are not limited thereto.

Unless otherwise stated, the term "substituted or unsubstituted", as used herein, means that substitution is substituted by at least one substituent selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophen group, a $C_6$-$C_{20}$ arylthiophen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited thereto.

Unless otherwise expressly stated, the Formula used in the present invention, as used herein, is applied in the same manner as the substituent definition according to the definition of the exponent of the following Formula:

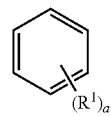

wherein, when a is an integer of 0, the substituent $R^1$ is absent, when a is an integer of 1, the sole substituent $R^1$ is linked to any one of the carbon constituting the benzene ring, when a is an integer of 2 or 3, each substituent $R^1$'s may be the same and different, when a is an integer of 4 to 6, and is linked to the benzene ring in a similar manner, whereas the indication of hydrogen bound to the carbon forming the benzene ring is omitted.

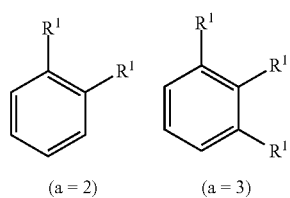

Hereinafter, a compound according to an aspect of the present invention and an organic electronic element comprising the same will be described.

The present invention provides a compound represented by Formula (1).

Formula (1)

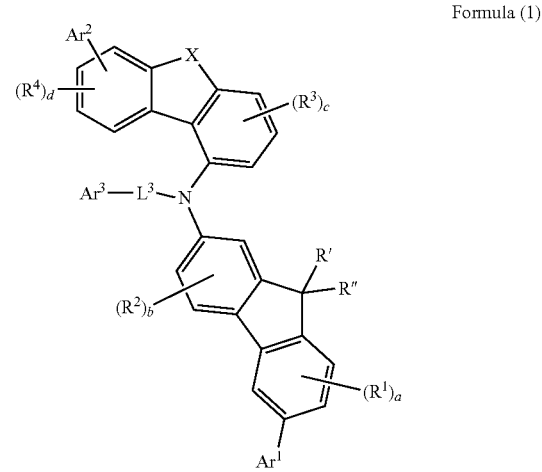

In Formula (1), each symbol may be defined as follows:
$R^1$, $R^2$, $R^3$ and $R^4$ are each independently the same or different, and each independently selected from the group consisting of a hydrogen; deuterium; halogen; an $C_6$-$C_{60}$ aryl group; fluorenyl group; a $C_2$-$C_{60}$ heterocyclic group including at least one heteroatom of O, N, S, Si or a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;
wherein in case $R^1$, $R^2$, $R^3$ and $R^4$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, wherein in case $R^1$, $R^2$, $R^3$ and $R^4$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc., wherein in case $R^1$, $R^2$, $R^3$ and $R^4$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case $R^1$, $R^2$, $R^3$ and $R^4$ are an aliphatic ring group, it may be preferably a $C_3$-$C_{30}$ aliphatic ring, and more preferably a $C_3$-$C_{24}$ aliphatic ring, wherein in case $R^1$, $R^2$, $R^3$ and $R^4$ are an alkyl group, it may be preferably a $C_1$-$C_{30}$ alkyl group, and more preferably a $C_1$-$C_{24}$ alkyl group, wherein in case $R^1$, $R^2$, $R^3$ and $R^4$ are alkoxyl groups, it may be preferably $C_1$-$C_{24}$ alkoxyl groups, wherein in case $R^1$, $R^2$, $R^3$ and $R^4$ are an aryloxy group, it may be preferably an $C_6$-$C_{24}$ aryloxy group, a, b, c and d are each independently an integer of 0 to 3, R', R" and $Ar^1$ are each independently selected from the group consisting of an $C_6$-$C_{60}$ aryl group; fluorenyl group; a $C_2$-$C_{60}$ heterocyclic group including at least one heteroatom of O, N, S, Si or P, a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or R' and R" can be bonded to each other to form a ring, $Ar^2$ are each independently selected from the group consisting of a hydrogen; deuterium; an $C_6$-$C_{60}$ aryl group; fluorenyl group; a $C_2$-$C_{60}$ heterocyclic group including at least one heteroatom of O, N, S, Si or P, a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

wherein in case R', R", $Ar^1$ and $Ar^2$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, wherein in case R', R", $Ar^1$ and $Ar^2$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc., wherein in case R', R", $Ar^1$ and $Ar^2$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case R', R", $Ar^1$ and $Ar^2$ are an alkyl group, it may be preferably a $C_1$-$C_{30}$ alkyl group, and more preferably a $C_1$-$C_{24}$ alkyl group, wherein in case R', R", $Ar^1$ and $Ar^2$ are alkoxyl groups, it may be preferably $C_1$-$C_{24}$ alkoxyl groups, wherein in case R', R", $Ar^1$ and $Ar^2$ are an aryloxy group, it may be preferably an $C_6$-$C_{24}$ aryloxy group, $Ar^3$ are an $C_6$-$C_{60}$ aryl group; fluorenyl group; or a substituent represented by any of the following Formulas Ar-1 to Ar-6;

wherein in case $Ar^3$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, X is O or S, $L^3$ is each independently selected from the group consisting of a single bond; a $C_6$-$C_{60}$ arylene group; fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

wherein in case $L^3$ is an arylene group, it may be preferably a $C_6$-$C_{30}$ arylene group, more preferably a $C_6$-$C_{25}$ arylene group, for example, phenylene, biphenylene, naphthylene, terphenylene, anthracenylene, etc., wherein in case $L^3$ is a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc., wherein in case $L^3$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring,

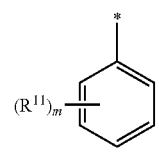

<Formula Ar-1>

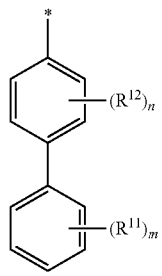

<Formula Ar-2>

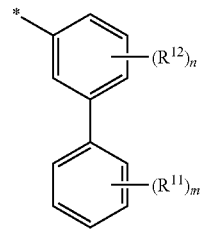

<Formula Ar-3>

-continued

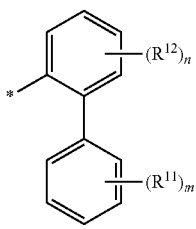
<Formula Ar-4>

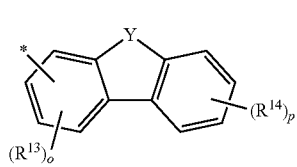
<Formula Ar-5>

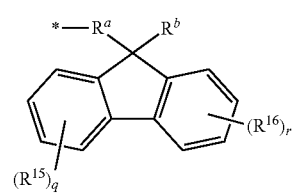
<Formula Ar-6> wherein:

$R^{11}$, $R^{12}$, $R^{13}$, $R^{14}$, $R^{15}$ and $R^{16}$ are the same as the definition of $R^1$, m is an integer of 0 to 5, n, p, q and r are each independently an integer of 0 to 4, o is an integer of 0 to 3, Y is O, S, $CR^xR^y$ or $NR^z$, $R^a$, $R^b$, $R^x$, $R^y$ and $R^z$ are the same as the definition of R', or $R^a$ and $R^b$, or $R^x$ and $R^y$ can be bonded to each other to form a ring,

* means a position to be bonded.

wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_5$-$C_{20}$ arylalkenyl group; and also the hydrogen of these substituents may be further substituted with one or more deuteriums, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the compound represented by Formula (1) is represented by any of the Formulas (2) to (5):

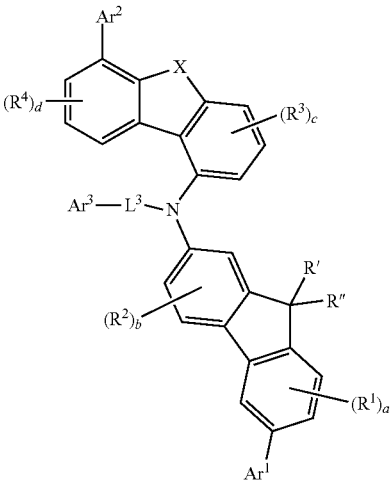
Formula (2)

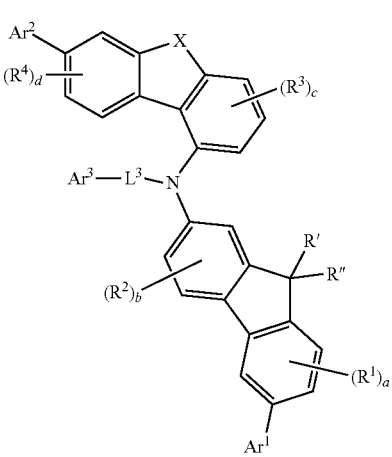
Formula (3)

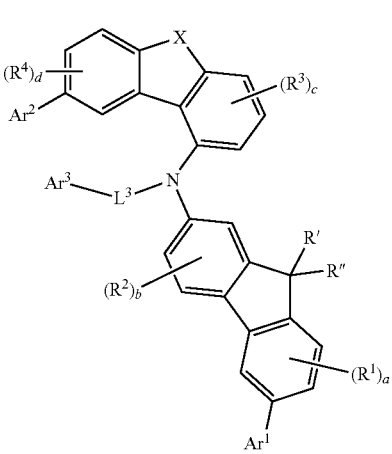
Formula (4)

-continued

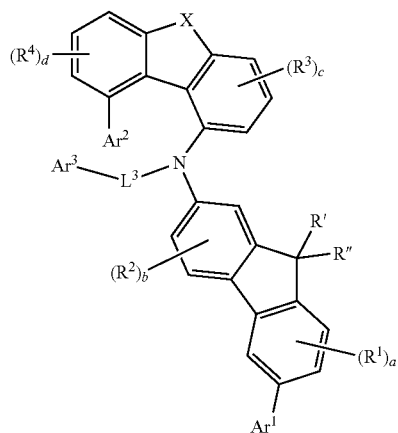

Formula (5)

wherein $R^1$, $R^2$, $R^3$, $R^4$, R', R", $Ar^1$, $Ar^2$, $Ar^3$, $L^3$, a, b, c and d are the same as defined in Formula (1).

Also, $Ar^3$ is represented by any one of Formulas Ar-1 to Ar-6.

Also, $L^3$ is represented by any one of Formulas L-1 to L-3.

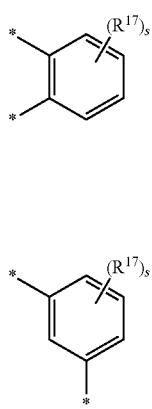

<Formula L-1>

<Formula L-2>

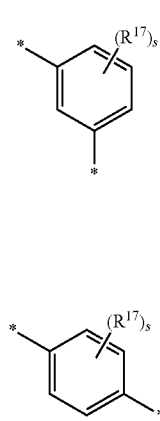

<Formula L-3> wherein, $R^{17}$ is the same as the definition of $R^1$ in Formula (1), s is an integer of 0 to 4,

* means a position to be bonded.

Specifically, the compound represented by Formula (1) may be any one of the following compounds P1-1 to P1-51, but is not limited thereto.

P1-1

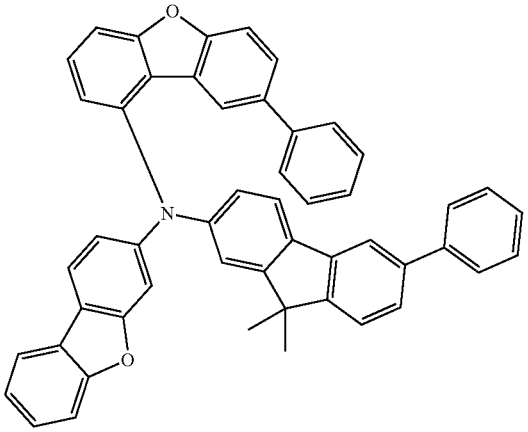

P1-2

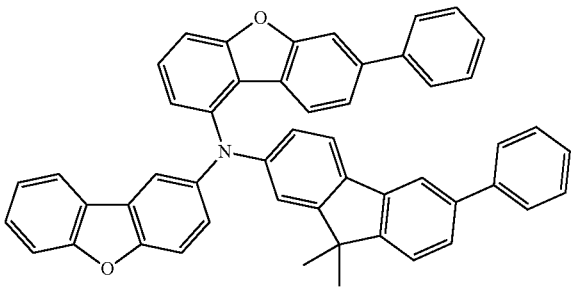

P1-3

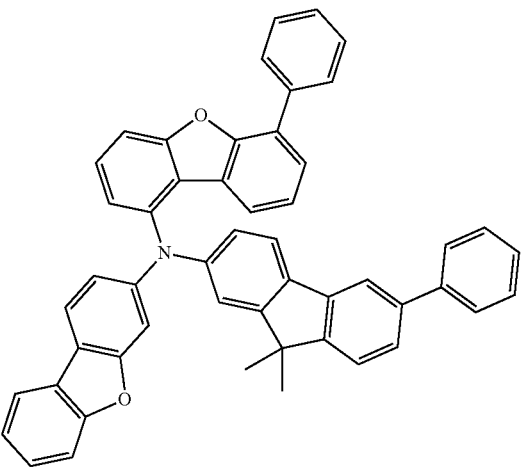

P1-4
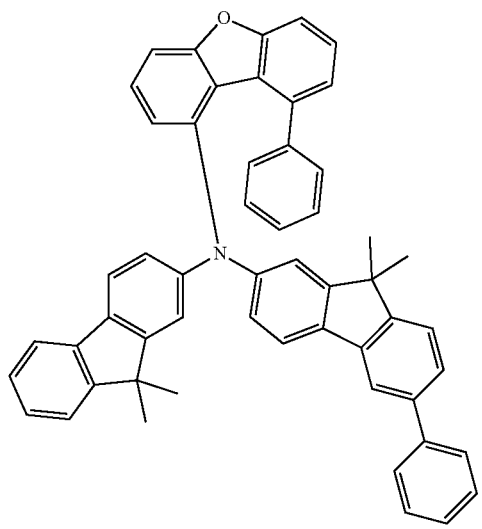
P1-5
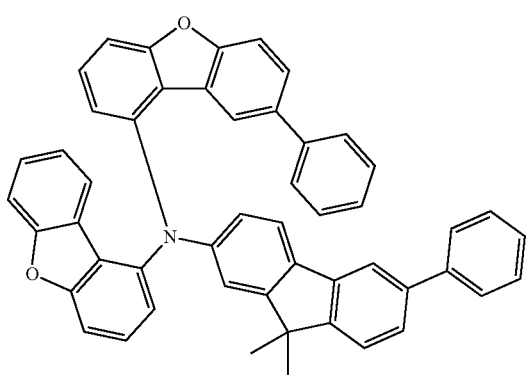
P1-6
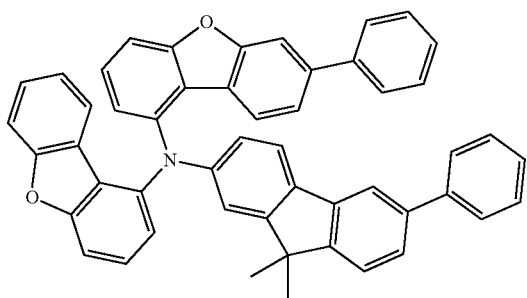
P1-7
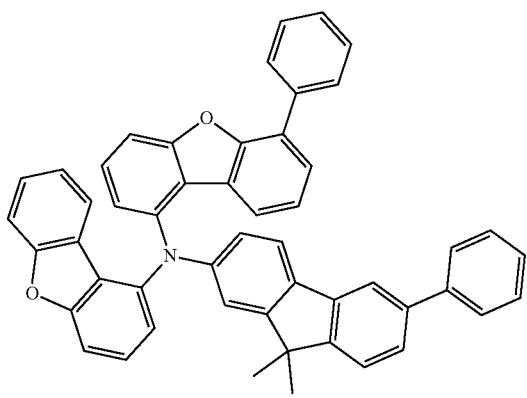
P1-8
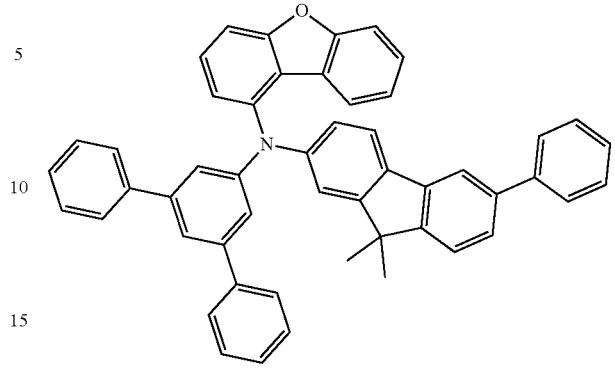
P1-9
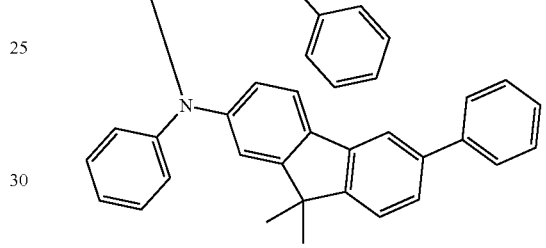
P1-10
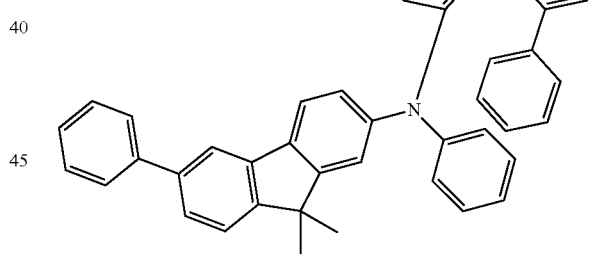
P1-11
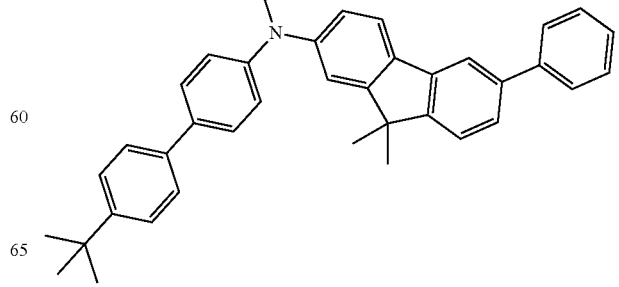

P1-12
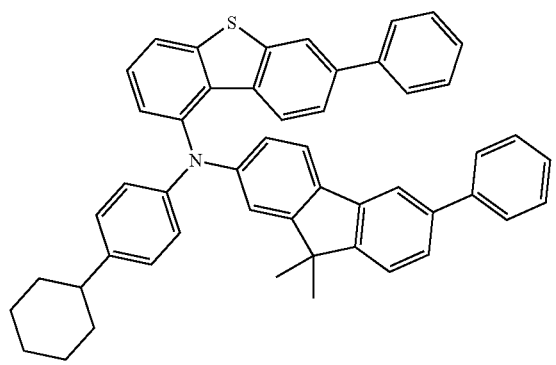
P1-13
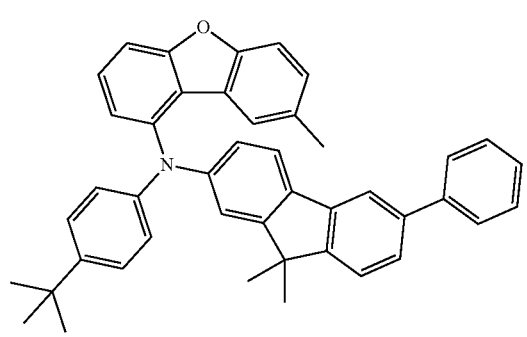
P1-14
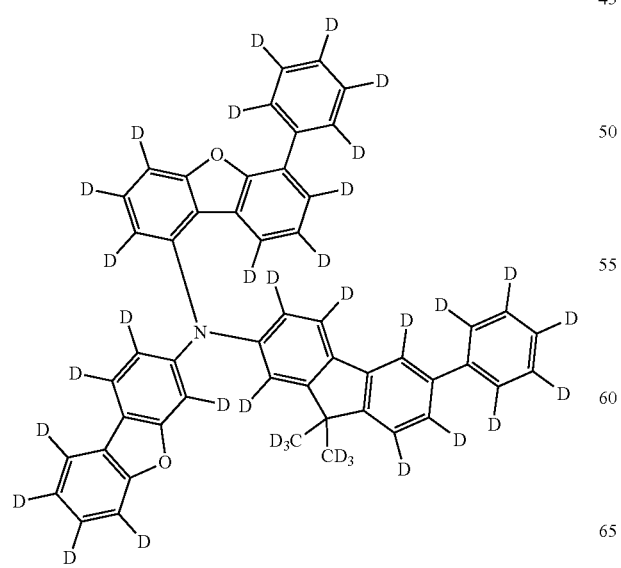
P1-15
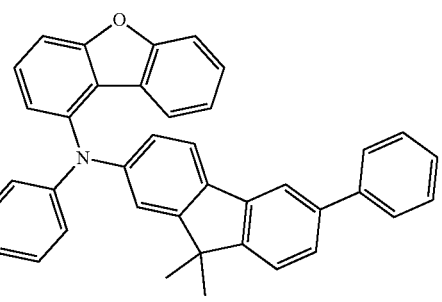
P1-16
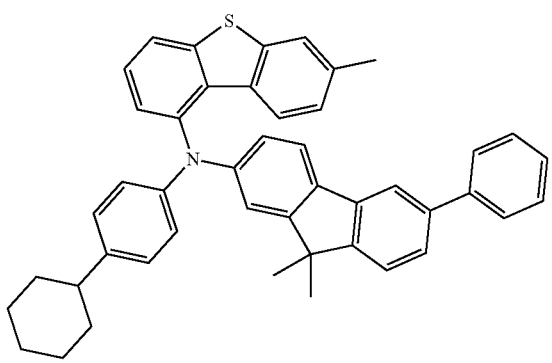
P1-17
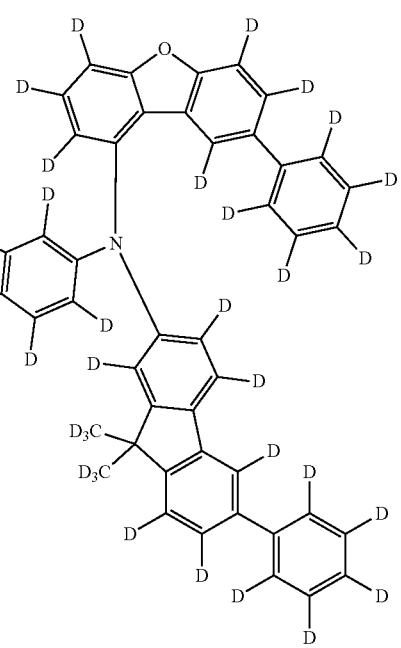

P1-18
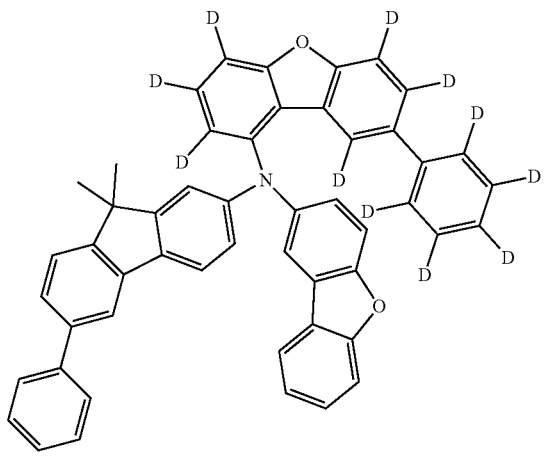
P1-19
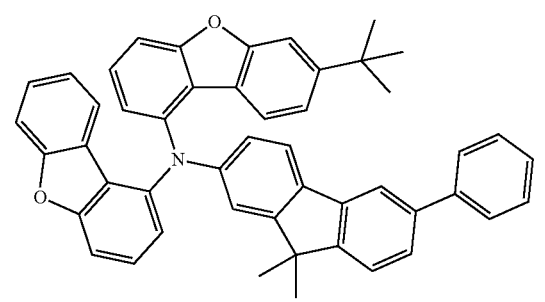
P1-20
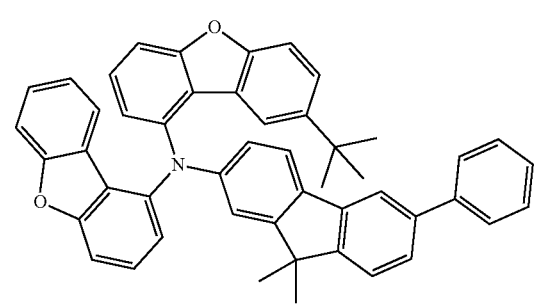
P1-21
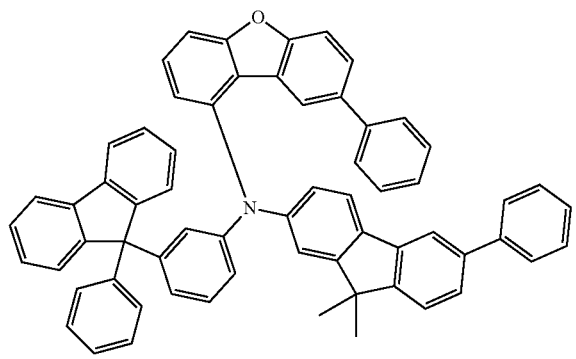
P1-22
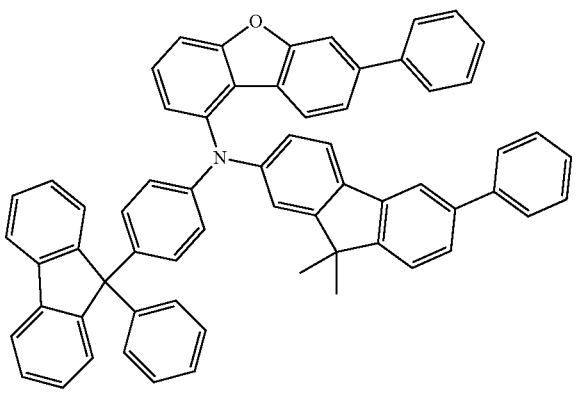
P1-23
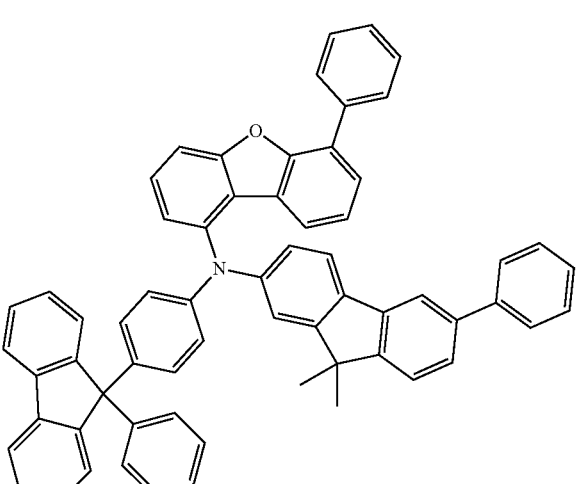
P1-24
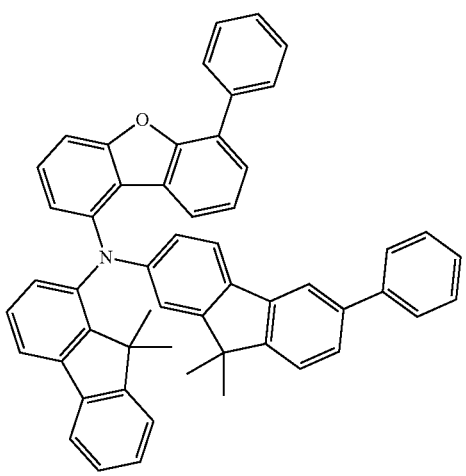

P1-25
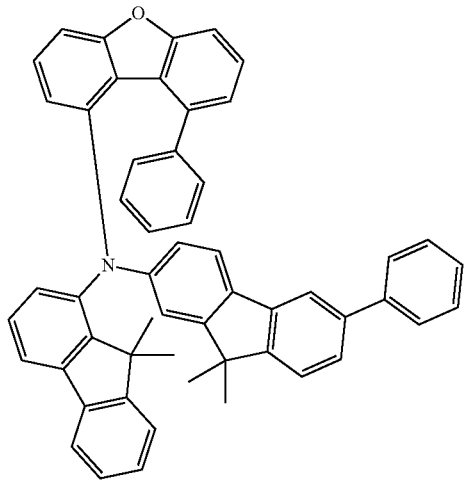
P1-26
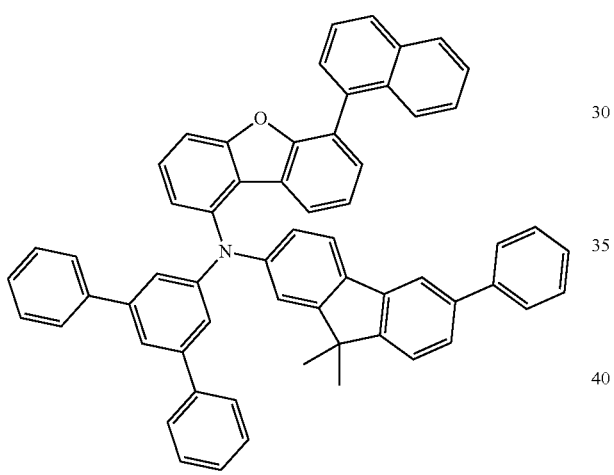
P1-27
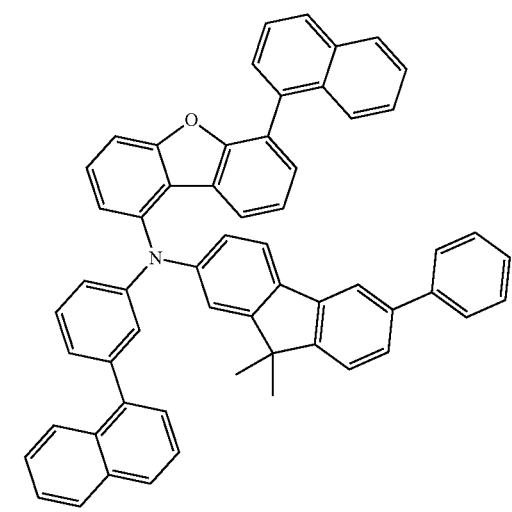
P1-28
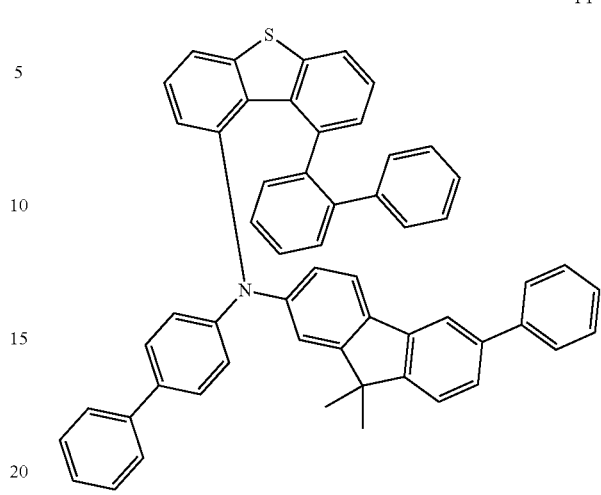
P1-29
P1-30
P1-31
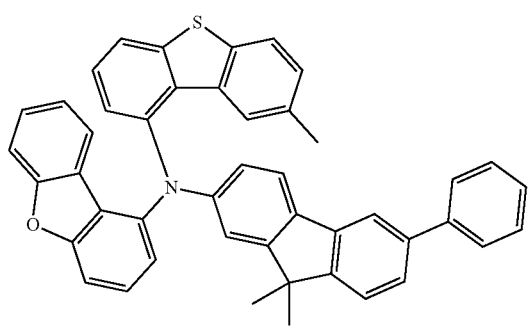

-continued
P1-32
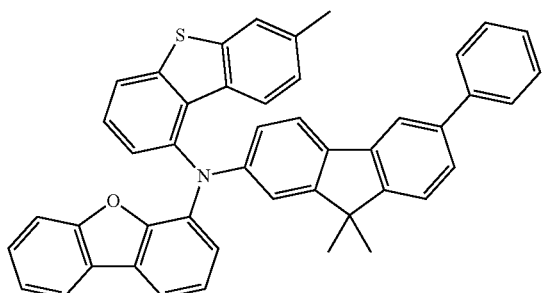
P1-33
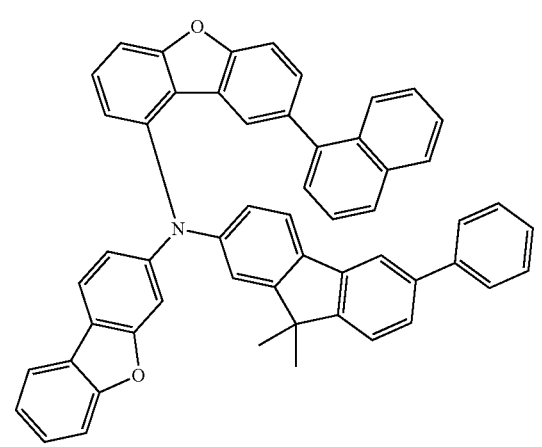
P1-34
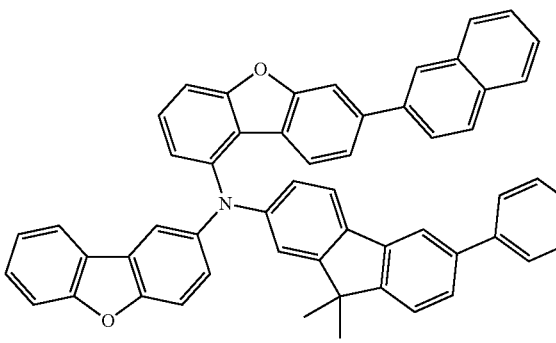
P1-35
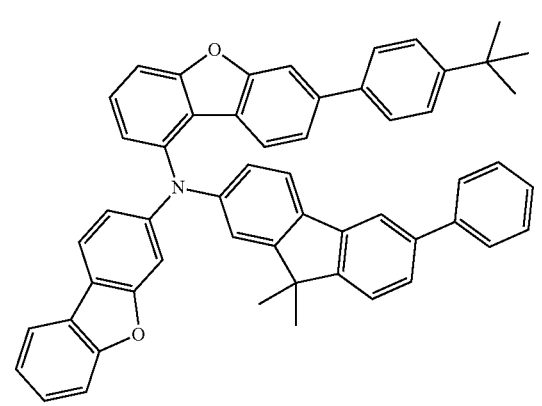
-continued
P1-36
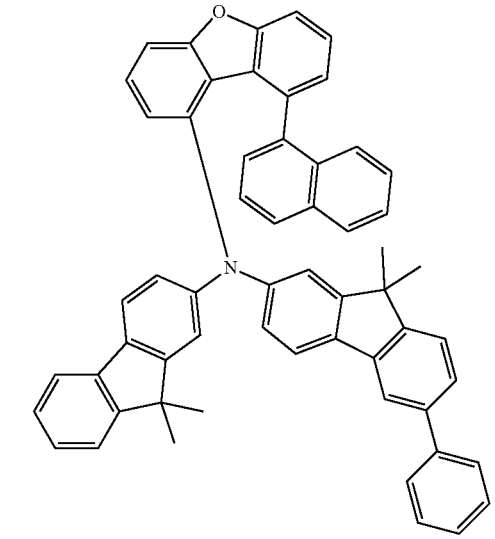
P1-37
P1-38
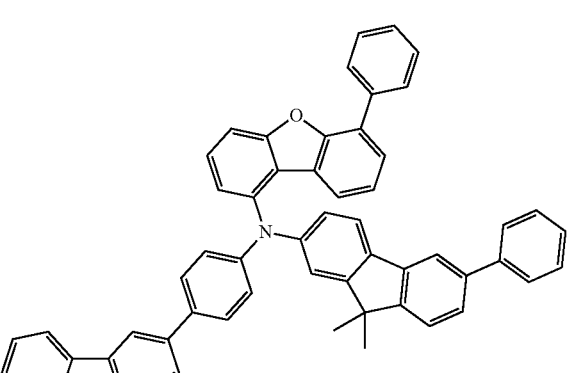
P1-39
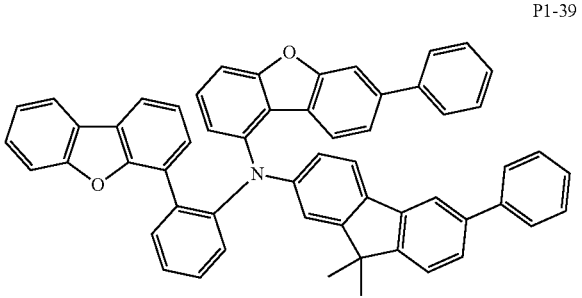

P1-40
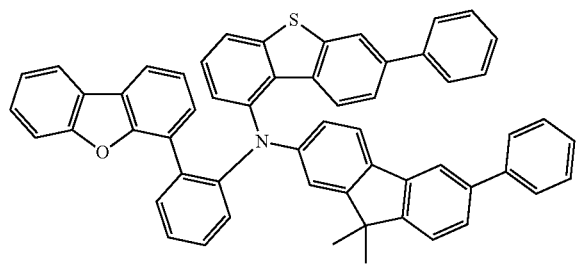
P1-41
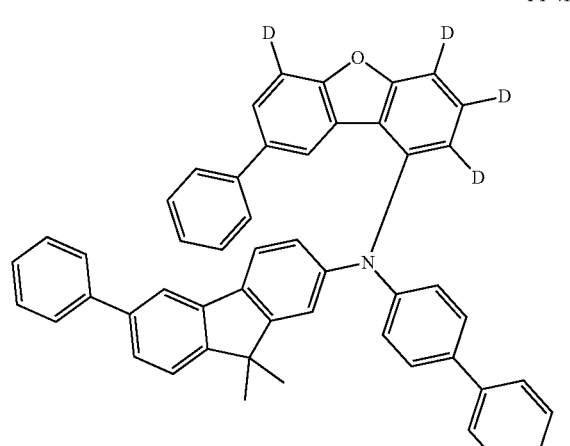
P1-42
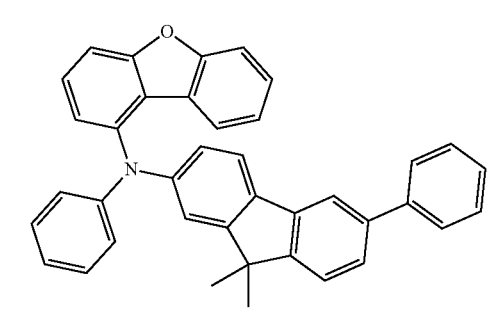
P1-43
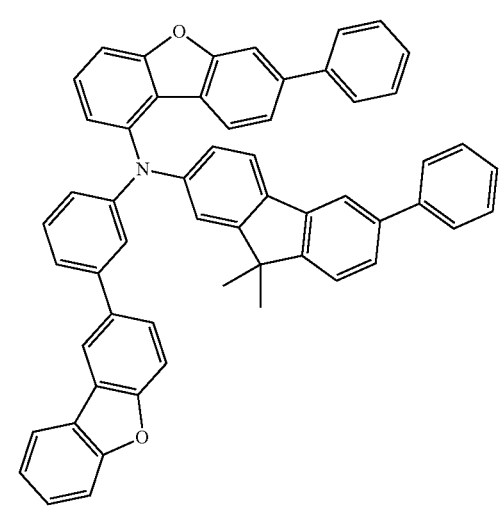
P1-44
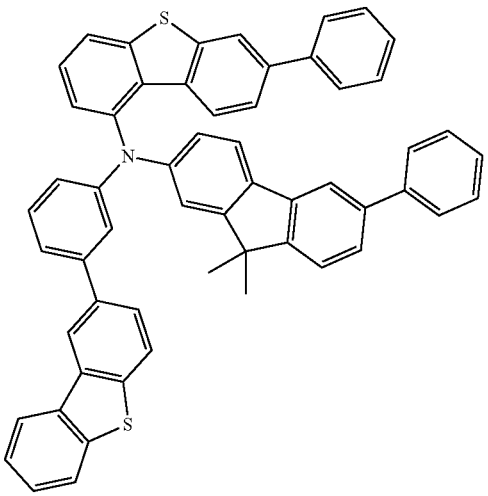
P1-45
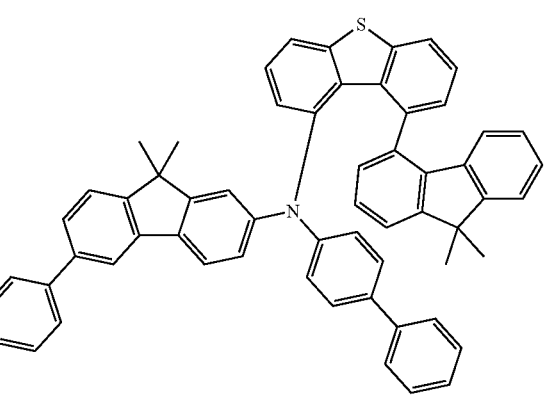
P1-46
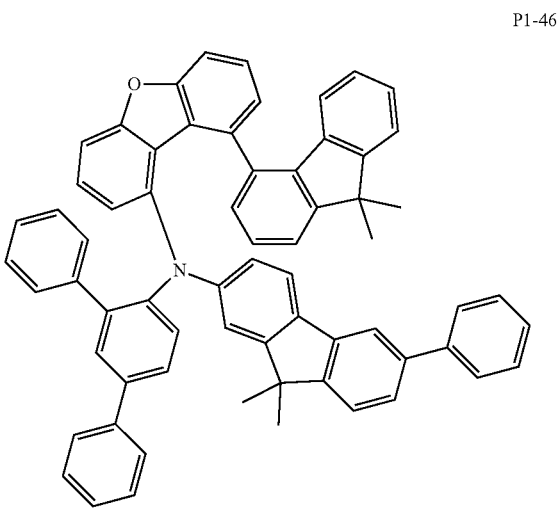

-continued

P1-47
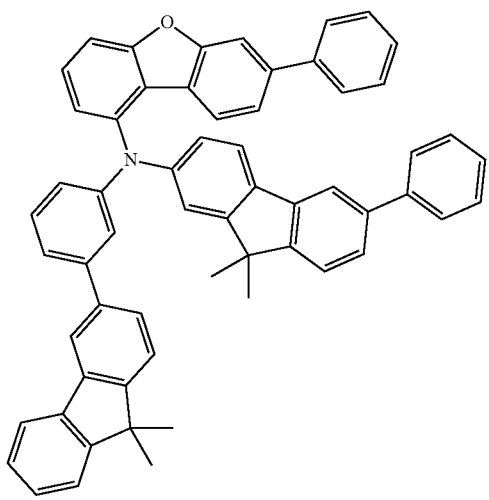

P1-48
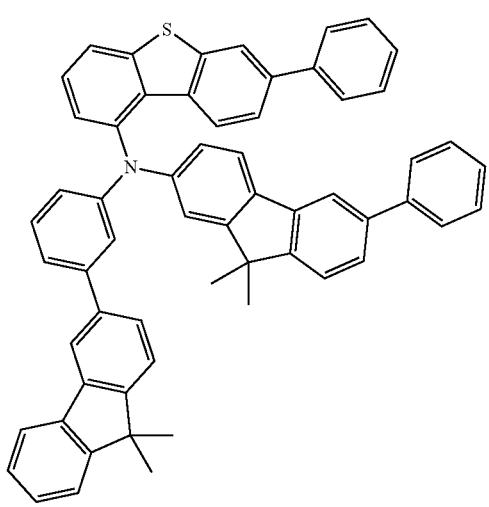

P1-49
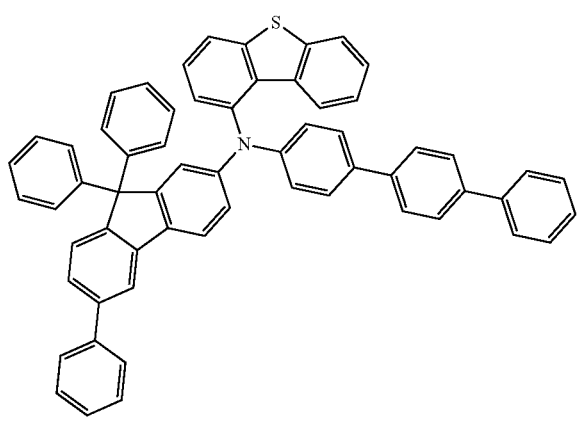

-continued

P1-50
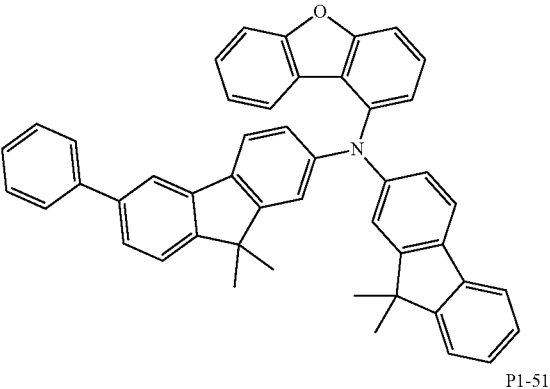

P1-51
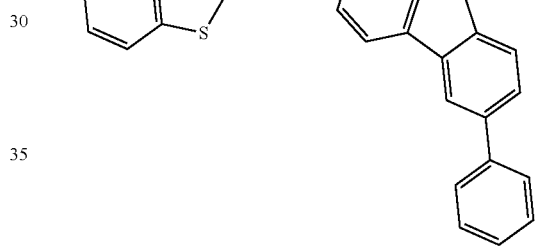

In another aspect, the present invention provides a method for reusing a compound by Formula (1) comprising:
recovering a crude organic light emitting material comprising the compound by Formula (1) from a deposition apparatus used in the process for depositing the organic emitting material to prepare an organic an organic light emitting device;
removing impurities from the crude organic light emitting material;
recovering the organic light emitting material after the impurities are removed; and
purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula (1) between the first electrode (110) and the second electrode (170). Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
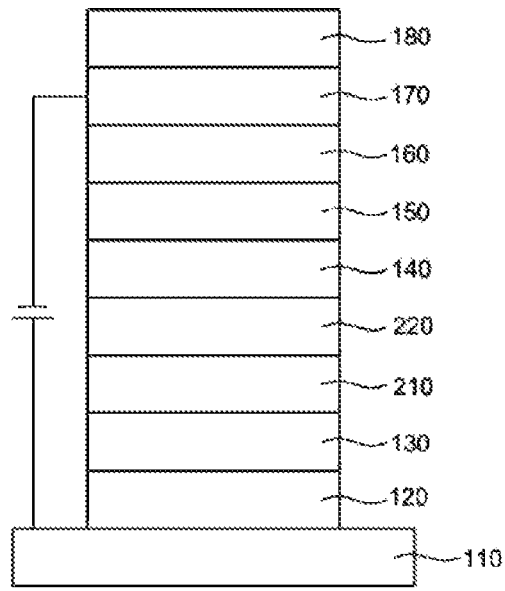

The organic material layer may sequentially comprise a hole injection layer (120), a hole transport layer (130), an emitting layer (140), an electron transport layer(150), and an electron injection layer (160) formed in sequence on the first electrode(110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the compound according to Formula (1) of the present invention can be used as a material for the emitting-auxiliary layer.

Figure 3:
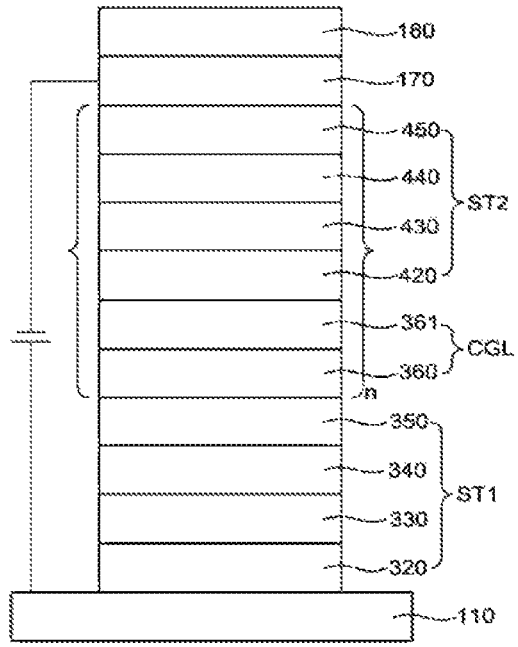
Figure 4:
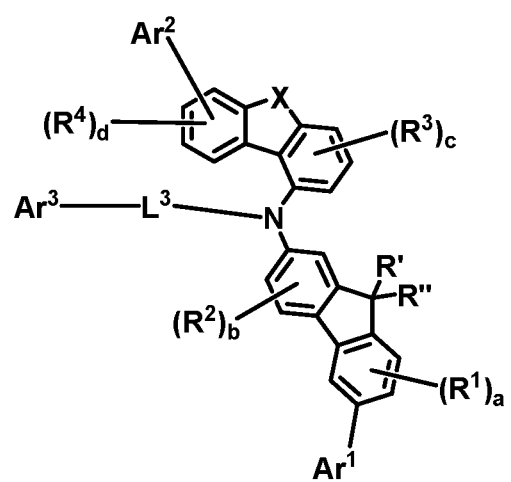
FIG. 4 shows a Formula according to one aspect of the present invention.

The organic material layer may include 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(120), the hole transport layer(130), the emitting layer (140), the electron transport layer(150), and the electron injection layer(160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula (1) to the organic material layer.

Also, the present invention provides a composition for an emitting-auxiliary layer comprising the compound represented by Formula (1), and provides an organic electronic element comprising the emitting-auxiliary layer.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis examples of the compound represented by Formula (1), and preparation examples of the organic electronic element of the present invention will be described in detail by way of example, but are not limited to the following examples.

SYNTHESIS EXAMPLE 1

The compound (final products) represented by Formula (1) according to the present invention is synthesized by reacting Sub1 and Sub 2 as shown in Reaction Scheme 1, but is not limited thereto.

I. Synthesis of Sub 1

Sub 1 of Reaction Scheme 1 may be synthesized through the reaction route of Reaction Scheme 2, but is not limited thereto.

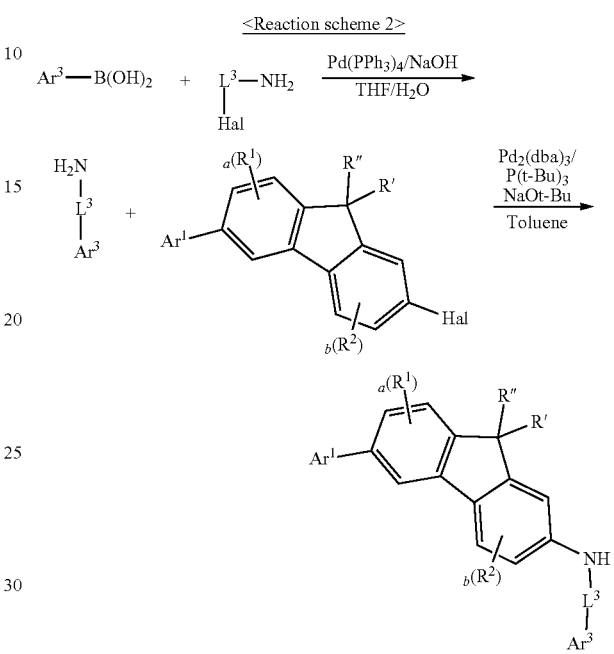

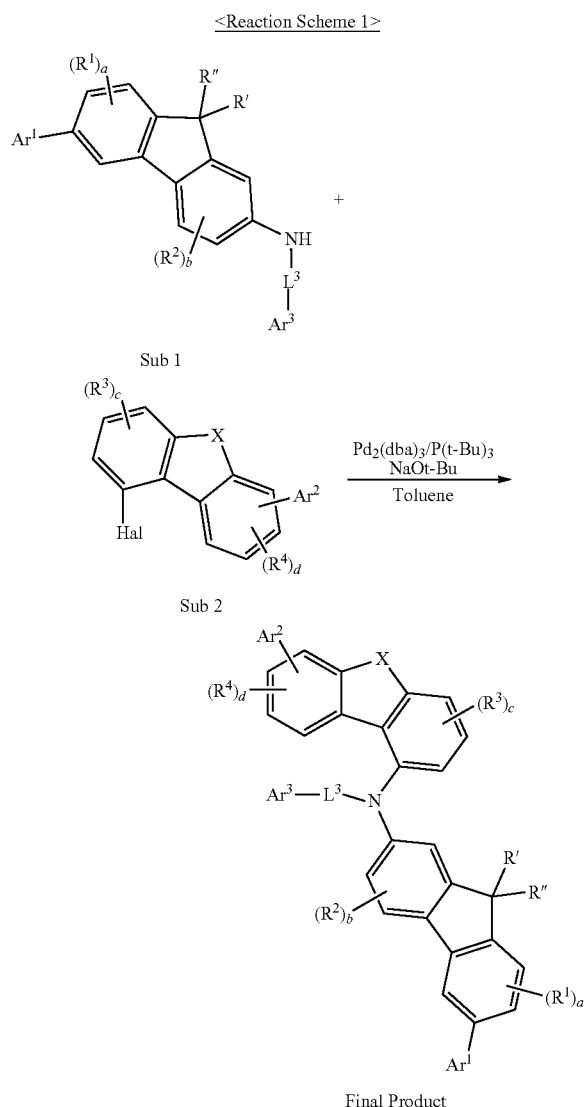

wherein,
Hal is I, Br or Cl,
$R^1$, $R^2$, $R^3$, $R^4$, R', R", $Ar^1$, $Ar^2$, $Ar^3$, $L^3$, a, b, c and d are the same as defined in Formula (1).

Synthesis examples of specific compounds belonging to Sub 1 are as follows.

Synthesis Example of Sub 1-131

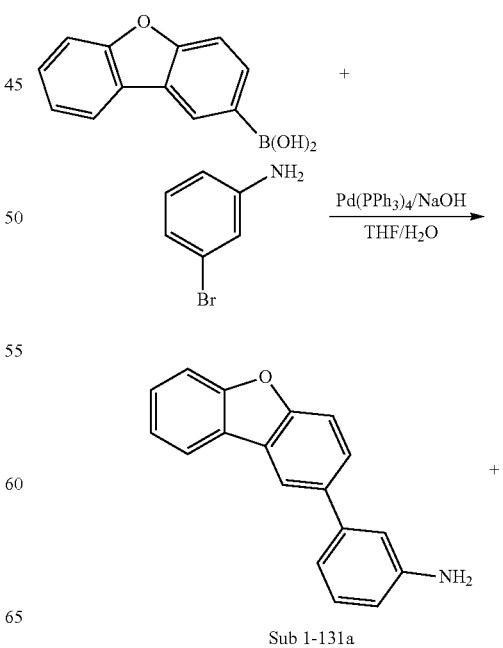

Sub 1-131a

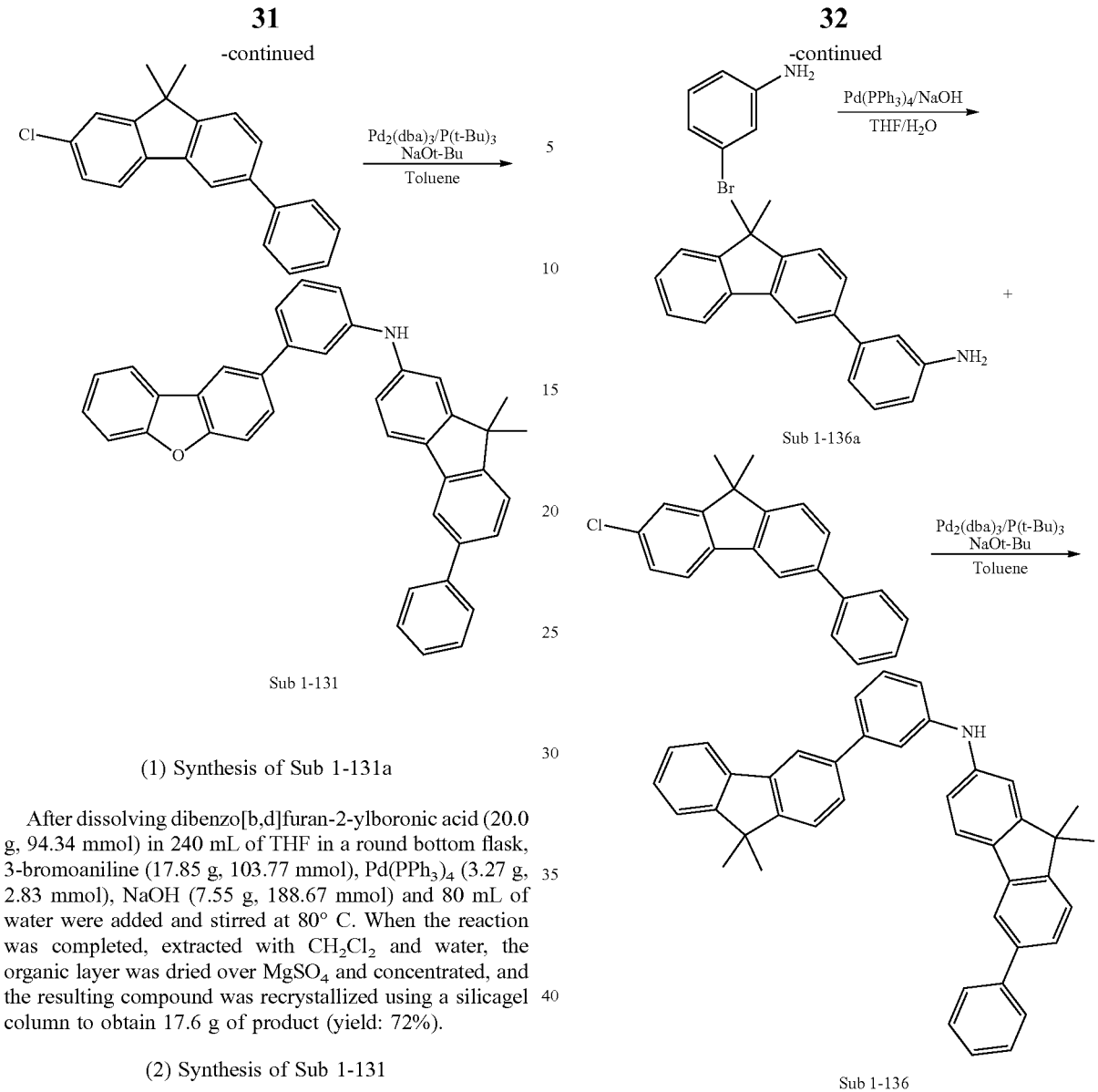

Sub 1-131

(1) Synthesis of Sub 1-131a

After dissolving dibenzo[b,d]furan-2-ylboronic acid (20.0 g, 94.34 mmol) in 240 mL of THF in a round bottom flask, 3-bromoaniline (17.85 g, 103.77 mmol), Pd(PPh$_3$)$_4$ (3.27 g, 2.83 mmol), NaOH (7.55 g, 188.67 mmol) and 80 mL of water were added and stirred at 80° C. When the reaction was completed, extracted with CH$_2$Cl$_2$ and water, the organic layer was dried over MgSO$_4$ and concentrated, and the resulting compound was recrystallized using a silicagel column to obtain 17.6 g of product (yield: 72%).

(2) Synthesis of Sub 1-131

The obtained Sub 1-131a (17.6 g, 67.87 mmol) was placed in a round bottom flask and dissolved in 230 mL of Toluene, then 2-chloro-9,9-dimethyl-6-phenyl-9H-fluorene (20.69 g, 67.87 mmol), Pd$_2$(dba)$_3$ (1.87 g, 2.04 mmol), P(t-Bu)$_3$ (0.82 g, 4.07 mmol), NaOt-Bu (13.05 g, 135.74 mmol) were added and stirred at room temperature. When the reaction was completed, extracted with Toluene and water, the organic layer was dried over MgSO$_4$ and concentrated, and the resulting compound was recrystallized using a silicagel column to obtain 25.1 g of product (yield: 70%).

Synthesis Example of Sub 1-136

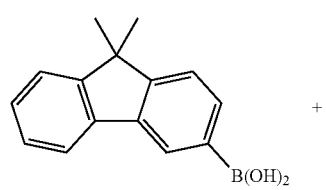

Sub 1-136

(1) Synthesis of Sub 1-136a

After dissolving (9,9-dimethyl-9H-fluoren-3-yl)boronic acid (20.0 g, 84.00 mmol) in 210 mL of THF in a round bottom flask, 3-bromoaniline (15.90 g, 92.40 mmol), Pd(PPh$_3$)$_4$ (2.91 g, 2.52 mmol), NaOH (6.72 g, 168.00 mmol) and 70 mL of water were added and stirred at 80° C. When the reaction was completed, extracted with CH$_2$Cl$_2$ and water, the organic layer was dried over MgSO$_4$ and concentrated, and the resulting compound was recrystallized using a silicagel column to obtain 16.4 g of product (yield: 68%).

(2) Synthesis of Sub 1-136

The obtained Sub 1-136a (16.4 g, 57.47 mmol) was placed in a round bottom flask and dissolved in 190 mL of Toluene, then 2-chloro-9,9-dimethyl-6-phenyl-9H-fluorene (17.52 g, 57.47 mmol), Pd$_2$(dba)$_3$ (1.58 g, 1.72 mmol), P(t-Bu)$_3$ (0.70 g, 3.45 mmol), NaOt-Bu (11.05 g, 114.93 mmol) were added and stirred at room temperature. When the reaction was completed, extracted with Toluene and water, the organic layer was dried over MgSO$_4$ and concentrated, and the resulting compound was recrystallized using a silicagel column to obtain 23.2 g of product (yield: 73%).

Synthesis Example of Sub 1-126

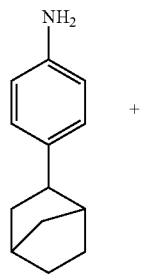

+

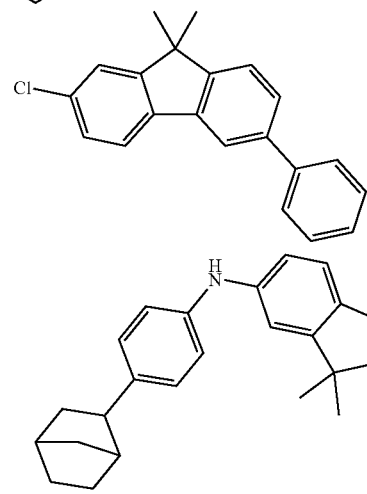

After dissolving 4-(bicyclo[2.2.1]heptan-2-yl)aniline (20 g, 106.79 mmol) in 356 mL of THF in a round bottom flask, 2-chloro-9,9-dimethyl-6-phenyl-9H-fluorene (32.55 g, 106.79 mmol), Pd$_2$(dba)$_3$ (2.93 g, 3.20 mmol), P(t-Bu)$_3$ (1.30 g, 6.41 mmol), NaOt-Bu (20.53 g, 213.57 mmol) were added and stirred at room temperature. When the reaction was completed, extracted with Toluene and water, the organic layer was dried over MgSO$_4$ and concentrated, and the resulting compound was recrystallized using a silicagel column to obtain 37.7 g of product (yield: 77%).

Examples of Sub 1 are as follows, but are not limited thereto.

Sub 1-115

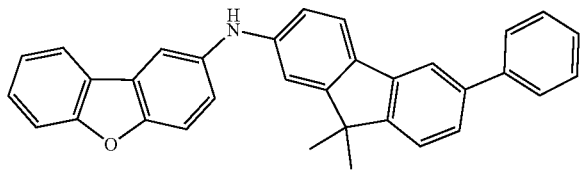

Sub 1-116

Sub 1-117

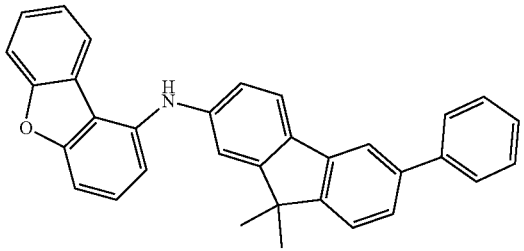

Sub 1-118

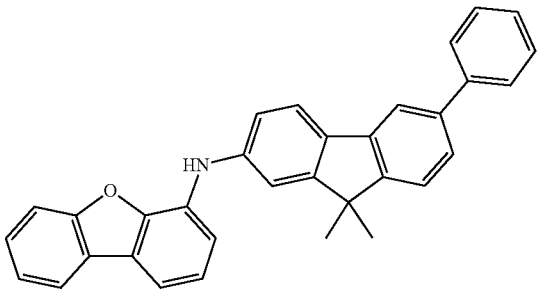

Sub 1-119

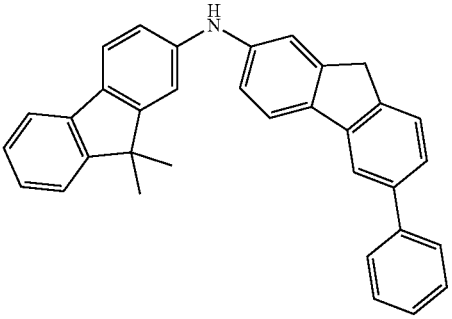

Sub 1-120

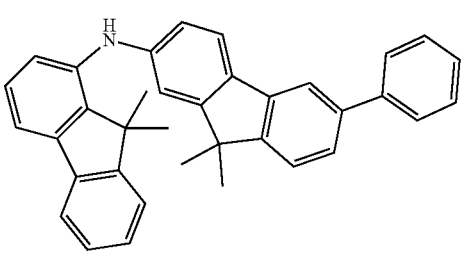

Sub 1-121

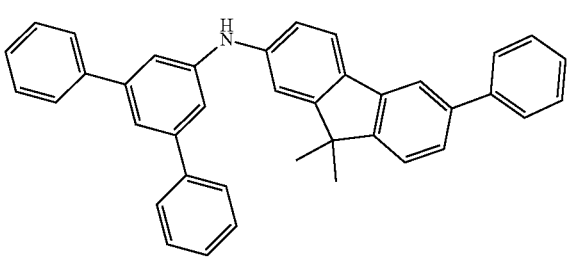

Sub 1-122
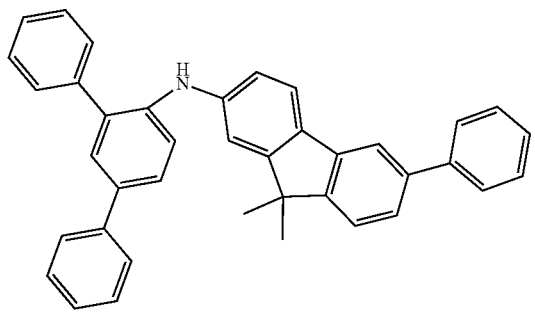
Sub 1-128
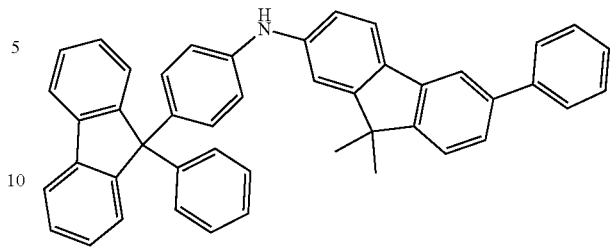
Sub 1-123
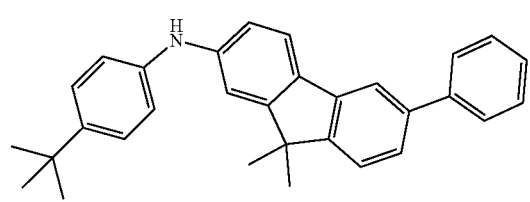
Sub 1-129
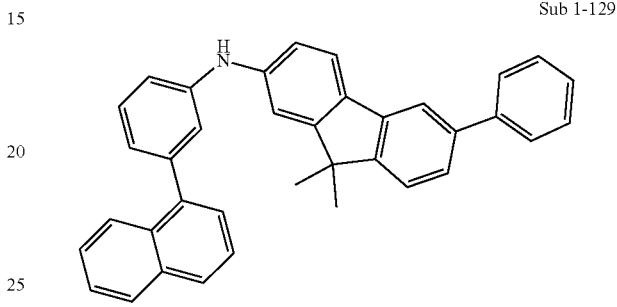
Sub 1-124
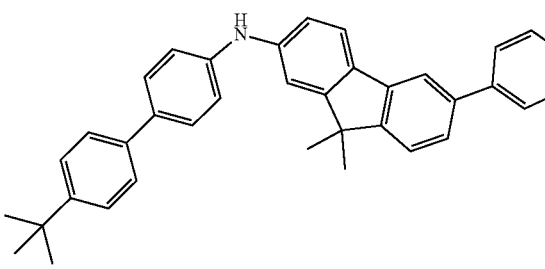
Sub 1-130
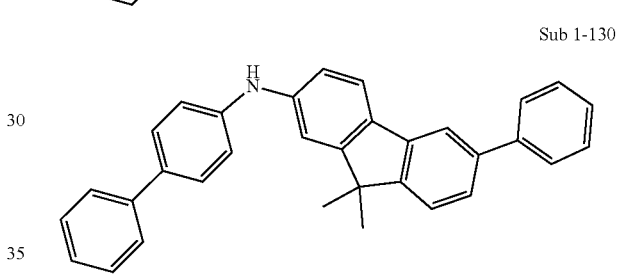
Sub 1-125
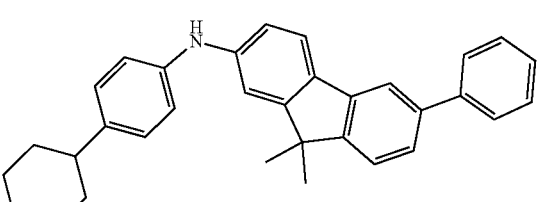
Sub 1-131
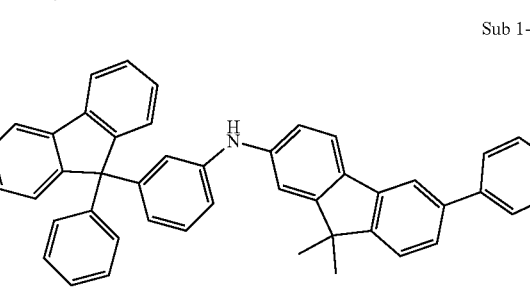
Sub 1-126
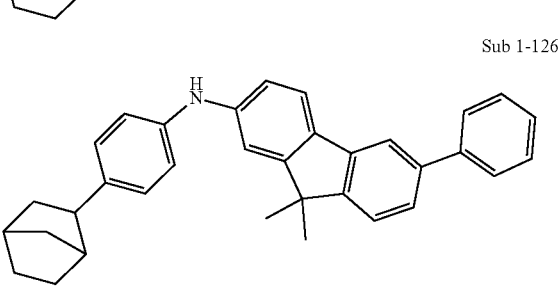
Sub 1-132
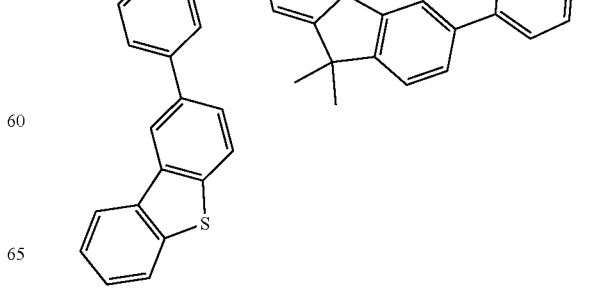
Sub 1-127

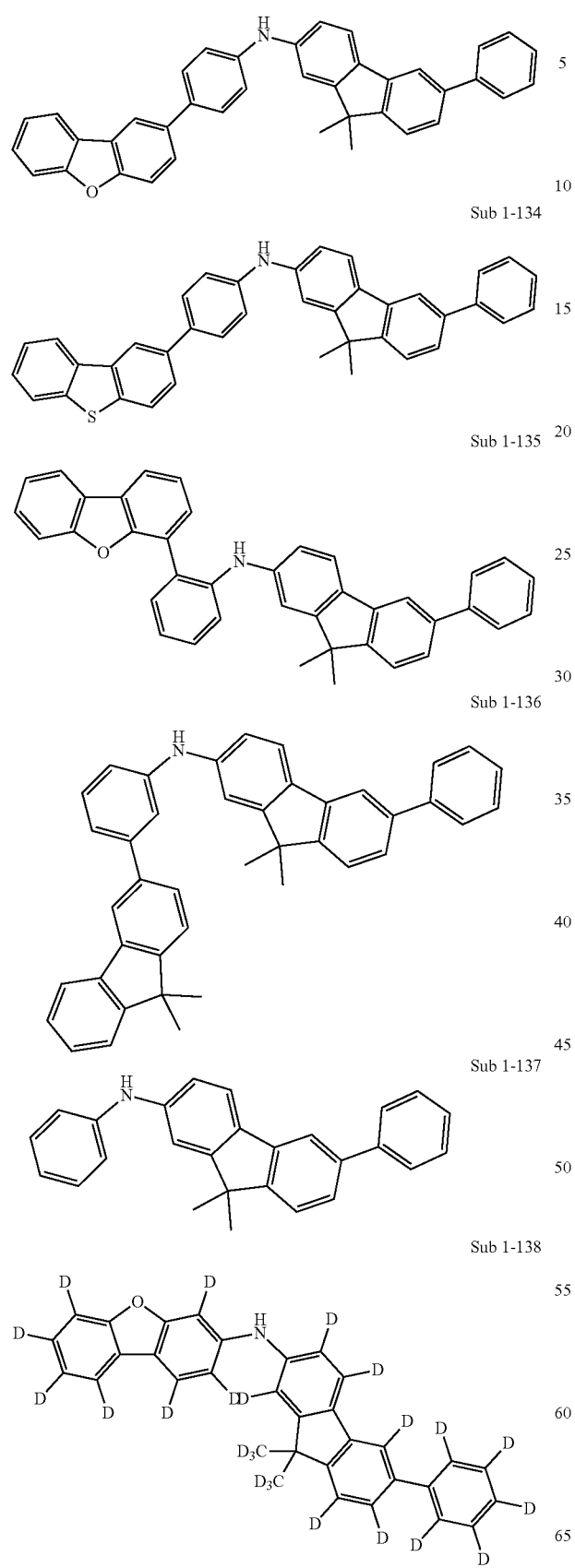
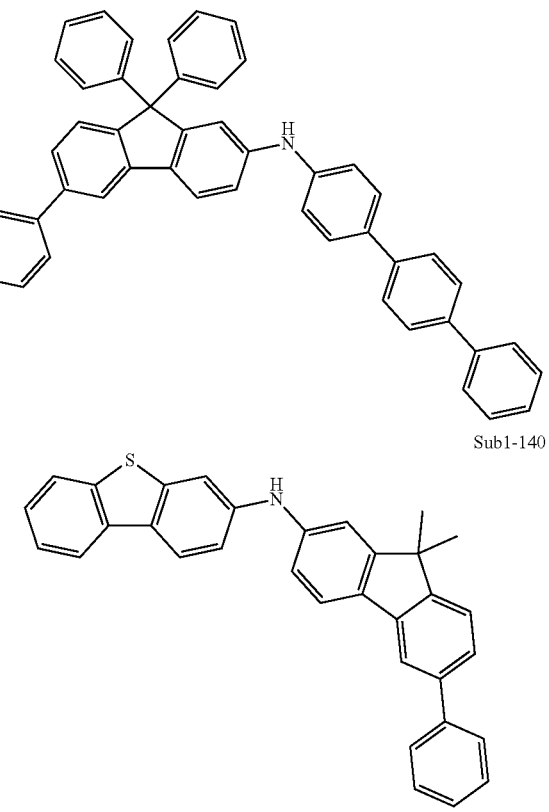

TABLE 1

| compound | FD-MS | compound | FD-MS |
|---|---|---|---|
| Sub 1-115 | m/z = 451.19 ($C_{33}H_{25}NO$ = 451.57) | Sub 1-116 | m/z = 451.19 ($C_{33}H_{25}NO$ = 451.57) |
| Sub 1-117 | m/z = 451.19 ($C_{33}H_{25}NO$ = 451.57) | Sub 1-118 | m/z = 451.19 ($C_{33}H_{25}NO$ = 451.57) |
| Sub 1-119 | m/z = 477.25 ($C_{36}H_{31}N$ = 477.65) | Sub 1-120 | m/z = 477.25 ($C_{36}H_{31}N$ = 477.65) |
| Sub 1-121 | m/z = 513.25 ($C_{39}H_{31}N$ = 513.68) | Sub 1-122 | m/z = 513.25 ($C_{39}H_{31}N$ = 513.68) |
| Sub 1-123 | m/z = 417.25 ($C_{31}H_{31}N$ = 417.60) | Sub 1-124 | m/z = 493.28 ($C_{37}H_{35}N$ = 493.69) |
| Sub 1-125 | m/z = 443.26 ($C_{33}H_{33}N$ = 443.63) | Sub 1-126 | m/z = 455.26 ($C_{34}H_{33}N$ = 455.64) |
| Sub 1-127 | m/z = 601.28 ($C_{46}H_{35}N$ = 601.79) | Sub 1-128 | m/z = 601.28 ($C_{46}H_{35}N$ = 601.79) |
| Sub 1-129 | m/z = 487.23 ($C_{37}H_{29}N$ = 487.65) | Sub 1-130 | m/z = 437.21 ($C_{33}H_{27}N$ = 437.59) |
| Sub 1-131 | m/z = 527.22 ($C_{39}H_{29}NO$ = 527.67) | Sub 1-132 | m/z = 543.20 ($C_{39}H_{29}NS$ = 543.73) |
| Sub 1-133 | m/z = 527.22 ($C_{39}H_{29}NO$ = 527.67) | Sub 1-134 | m/z = 543.20 ($C_{39}H_{29}NS$ = 543.73) |
| Sub 1-135 | m/z = 527.22 ($C_{39}H_{29}NO$ = 527.67) | Sub 1-136 | m/z = 553.28 ($C_{42}H_{35}N$ = 553.75) |
| Sub 1-137 | m/z = 361.18 ($C_{27}H_{23}N$ = 361.49) | Sub 1-138 | m/z = 475.34 ($C_{33}HD_{24}NO$ = 475.72) |
| Sub 1-139 | m/z = 637.28 ($C_{49}H_{35}N$ = 637.83) | Sub 1-140 | m/z = 467.17 ($C_{33}H_{25}NS$ = 467.63) |

II. Synthesis of Sub 2

Sub 2 of Reaction Scheme 1 may be synthesized by Reaction Scheme 3, but is not limited thereto.

<Reaction Scheme 3>

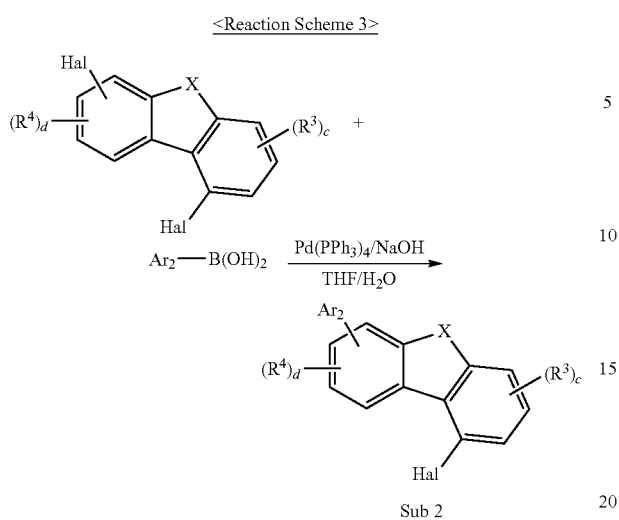

Sub 2 wherein,

Hal is I, Br or Cl,

R³, R⁴, X, Ar², c and d are the same as defined in Formula (1).

Examples of synthesis of specific compounds belonging to Sub 2 are as follows.

Synthesis Example of Sub 2-82

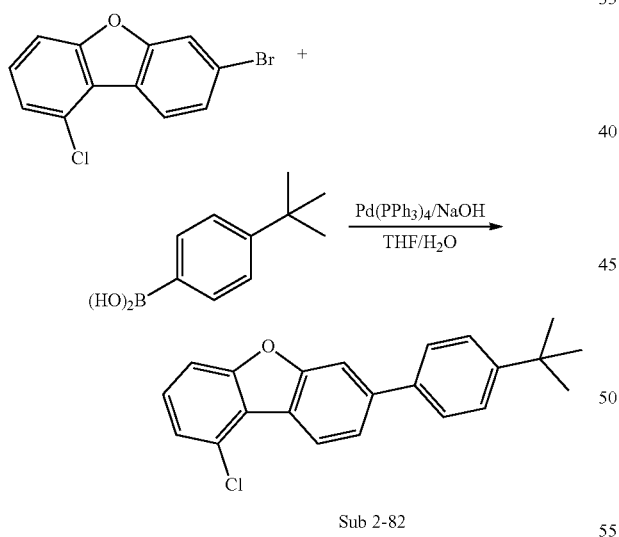

Sub 2-82

After dissolving 7-bromo-1-chlorodibenzo[b,d]furan (34.79 g, 123.57 mmol) in 280 mL of THF in a round bottom flask, (4-(tert-butyl)phenyl)boronic acid (20 g, 112.33 mmol), Pd(PPh₃)₄ (3.89 g, 3.37 mmol), NaOH (8.99 g, 224.67 mmol), and 94 mL of water were added and stirred at 80° C. When the reaction was completed, extracted with CH₂Cl₂ and water, the organic layer was dried over MgSO₄ and concentrated, and the resulting compound was recrystallized using a silicagel column to obtain 24.7 g of product (yield: 59%).

Synthesis Example of Sub 2-89

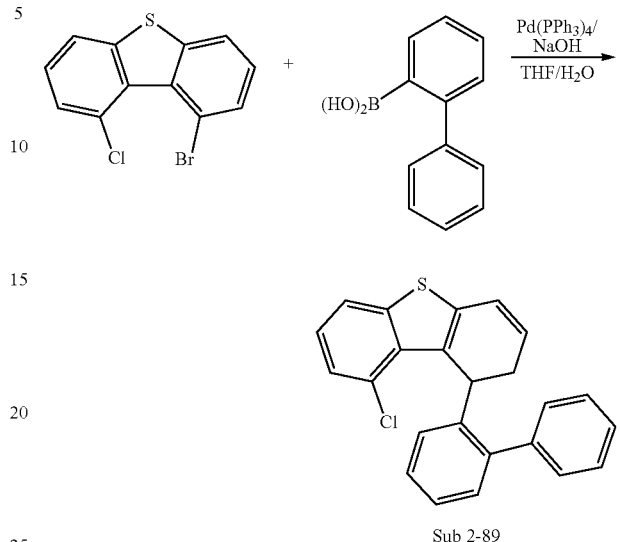

Sub 2-89

After dissolving 1-bromo-9-chlorodibenzo[b,d]thiophene (33.06 g, 111.09 mmol) in 250 mL of THF in a round bottom flask, [1,1'-biphenyl]-2-ylboronic acid (20 g, 100.99 mmol), Pd(PPh₃)₄ (3.50 g, 3.03 mmol), NaOH (8.08 g, 202.00 mmol), and 85 mL of water were added and stirred at 80° C. When the reaction was completed, extracted with CH₂Cl₂ and water, the organic layer was dried over MgSO₄ and concentrated, and the resulting compound was recrystallized using a silicagel column to obtain 23.8 g of product (yield: 63%).

Examples of Sub 2 are as follows, but are not limited thereto.

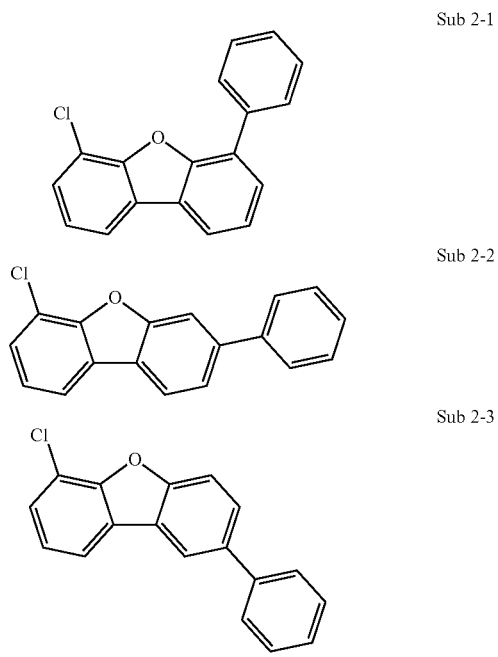

Sub 2-1

Sub 2-2

Sub 2-3

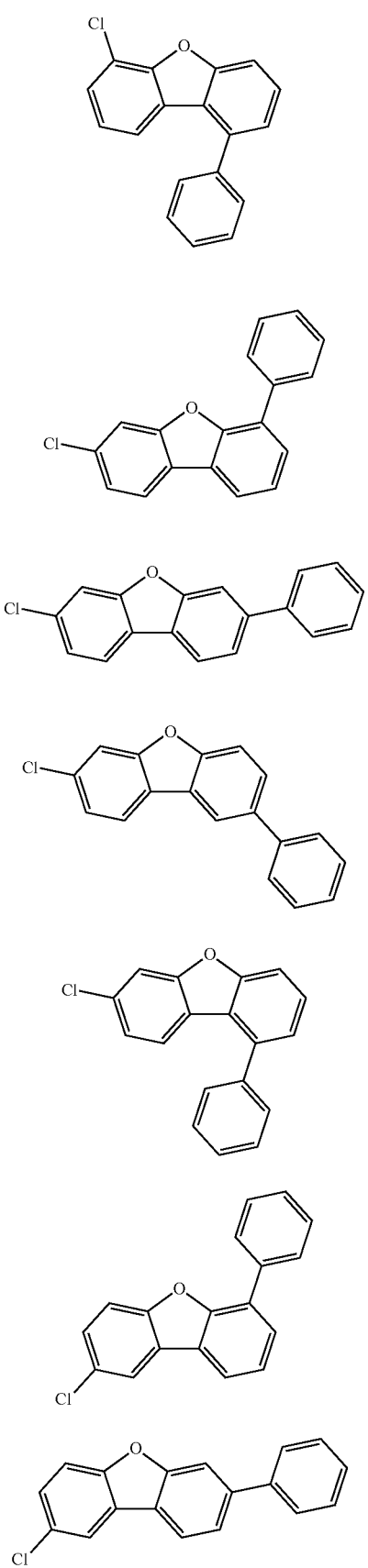
Sub 2-4
Sub 2-5
Sub 2-6
Sub 2-7
Sub 2-8
Sub 2-9
Sub 2-10
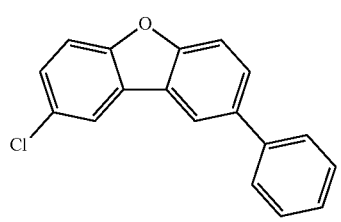
Sub 2-11
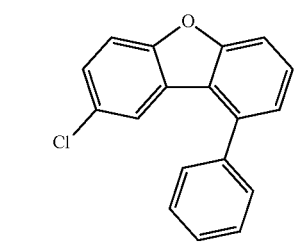
Sub 2-12
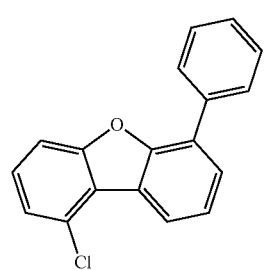
Sub 2-13
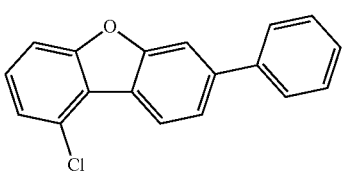
Sub 2-14
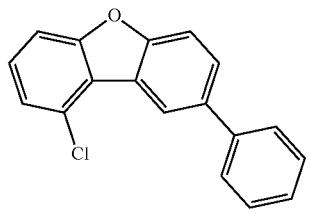
Sub 2-15
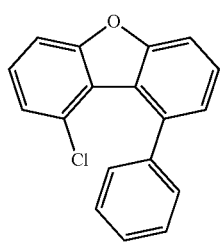
Sub 2-16
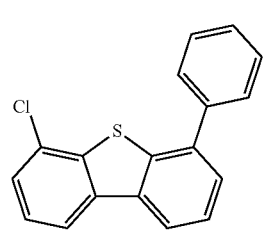
Sub 2-17

-continued
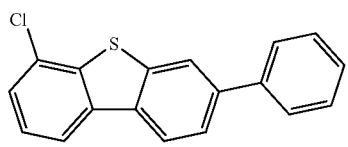
Sub 2-18
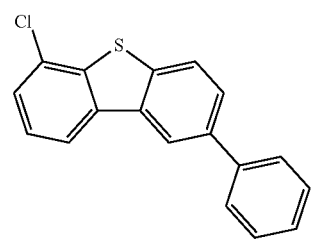
Sub 2-19
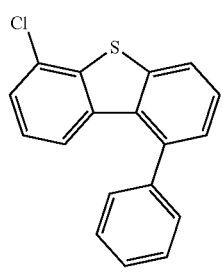
Sub 2-20
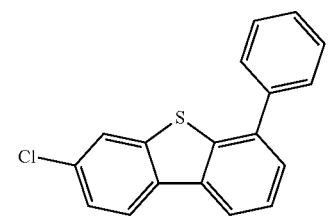
Sub 2-21
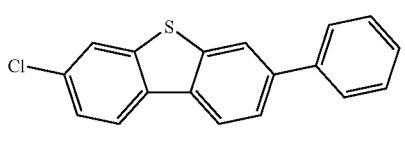
Sub 2-22
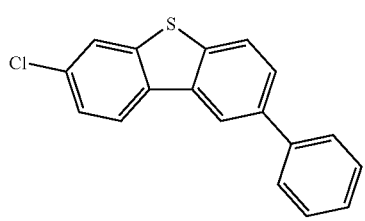
Sub 2-23
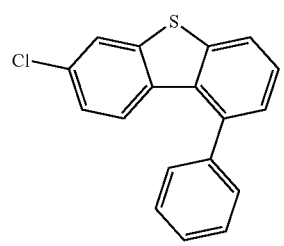
Sub 2-24
-continued
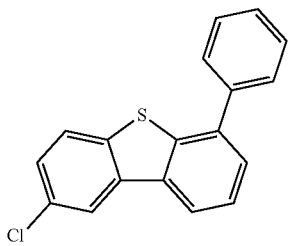
Sub 2-25
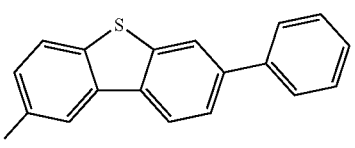
Sub 2-26
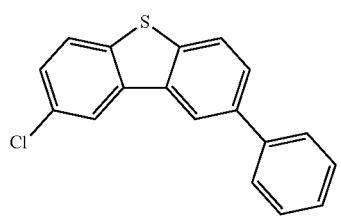
Sub 2-27
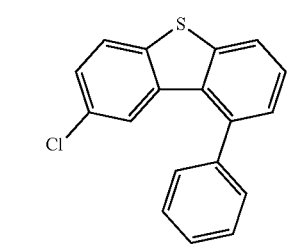
Sub 2-28
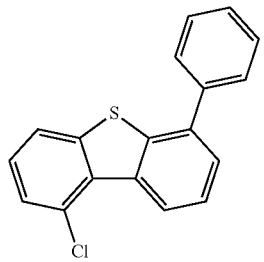
Sub 2-29
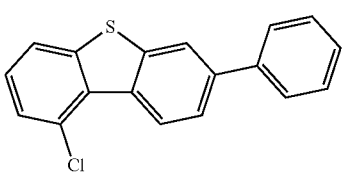
Sub 2-30
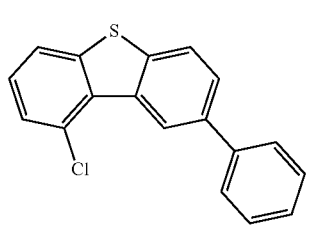
Sub 2-31

Sub 2-32
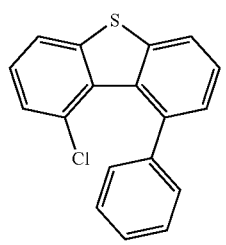
Sub 2-33
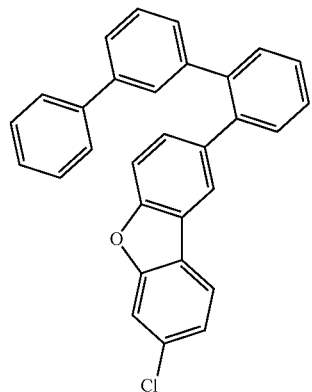
Sub 2-34
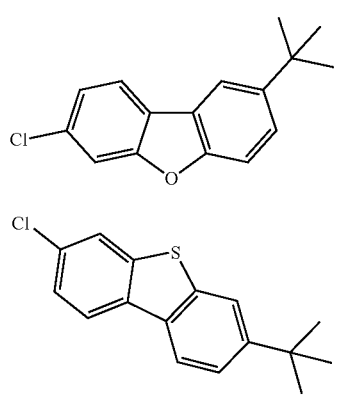
Sub 2-35
Sub 2-36
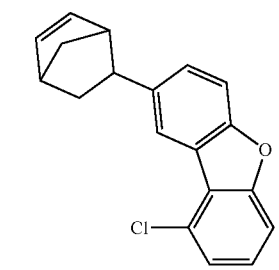
Sub 2-37
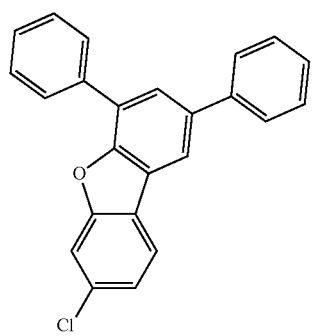
Sub 2-38
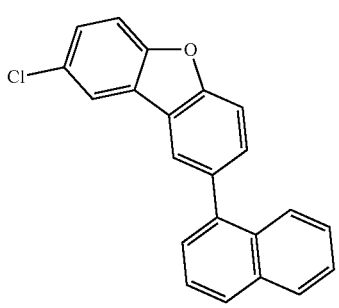
Sub 2-39
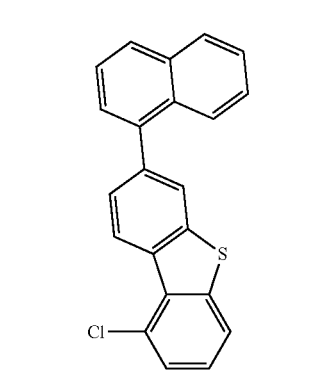
Sub 2-40
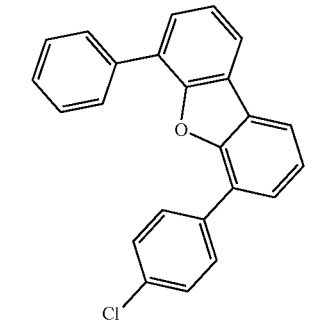
Sub 2-41
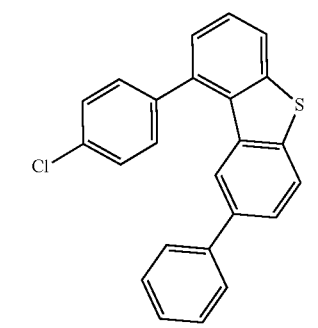
Sub 2-42
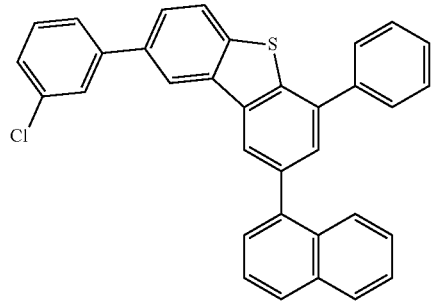

-continued
Sub 2-43
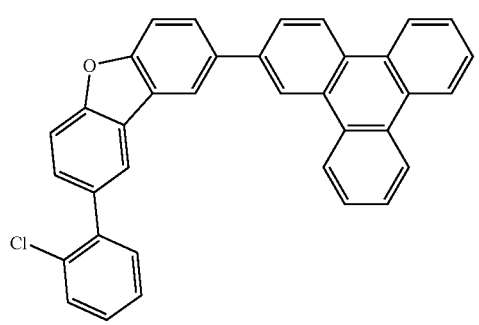
Sub 2-44
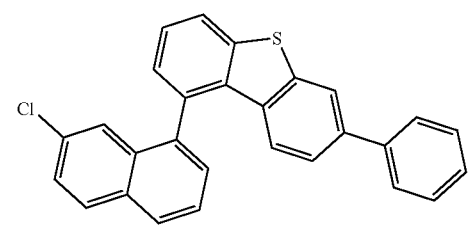
Sub 2-45
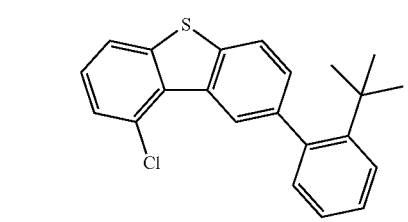
Sub-46
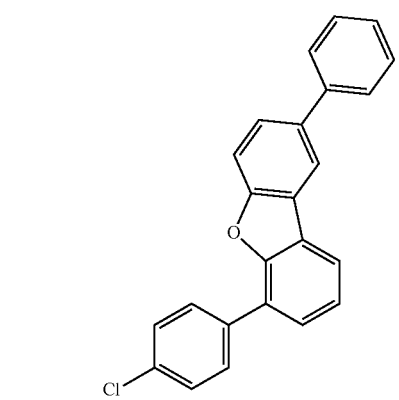
Sub 2-47
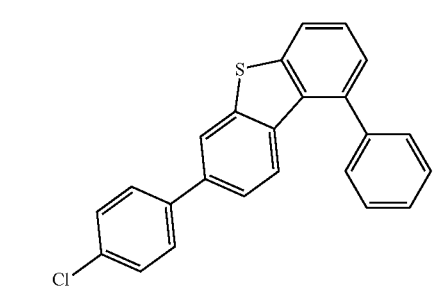
-continued
Sub 2-48
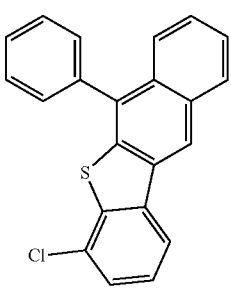
Sub 2-49
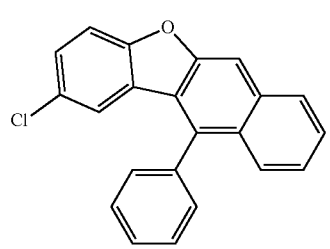
Sub 2-50
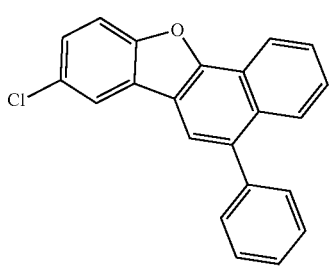
Sub 2-51
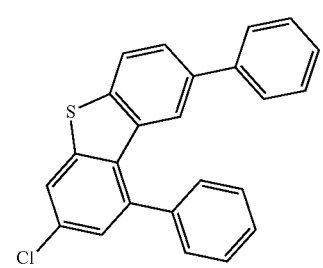
Sub 2-52
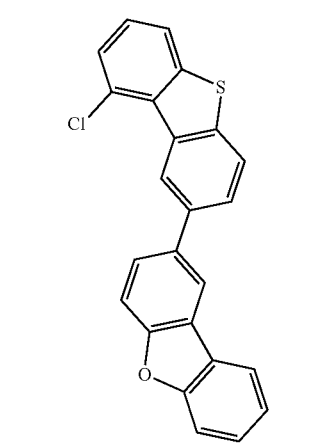

Sub 2-53
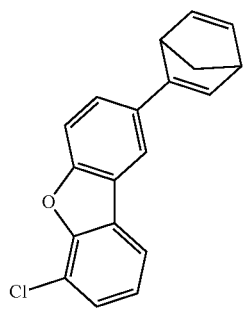
Sub 2-54
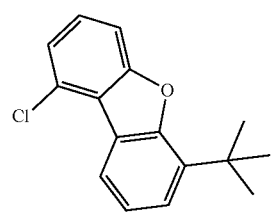
Sub 2-55
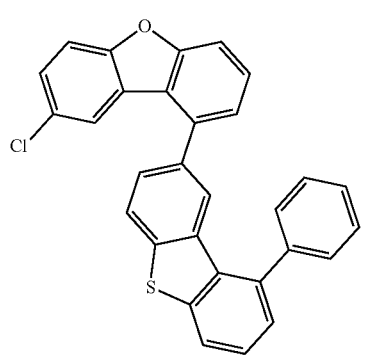
Sub 2-56
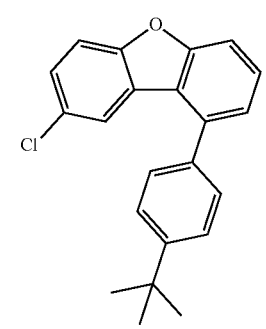
Sub 2-57
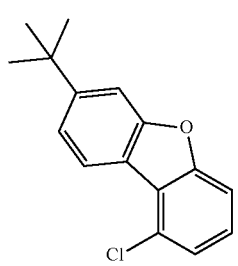
Sub 2-58
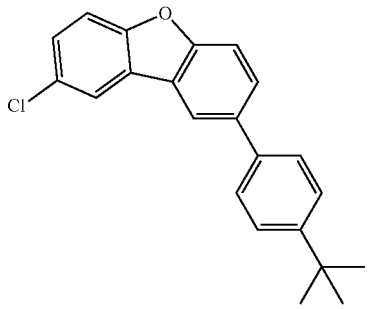
Sub 2-59
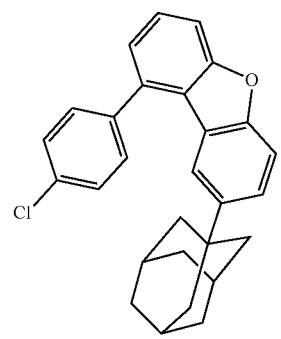
Sub 2-60
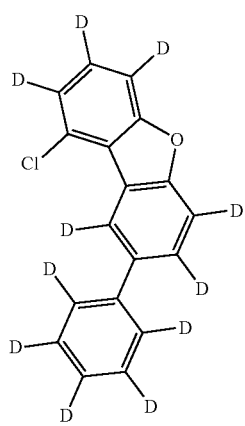
Sub 2-61
Sub 2-62
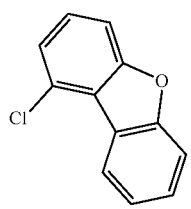

-continued
Sub 2-63
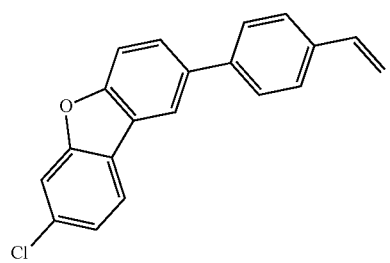
Sub 2-64
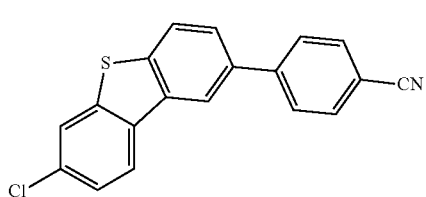
Sub 2-65
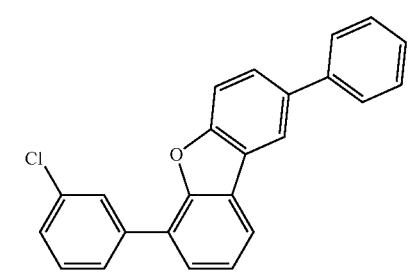
Sub 2-66
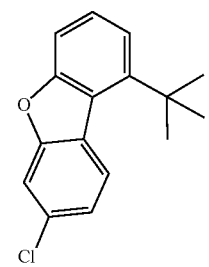
Sub 2-67
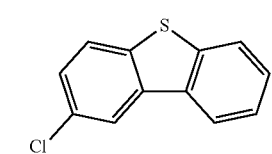
Sub 2-68
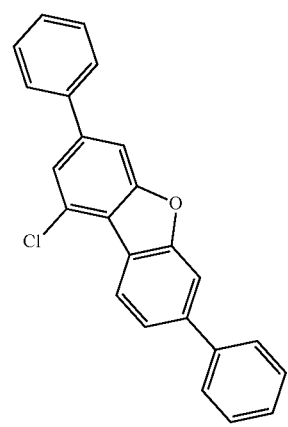
-continued
Sub 2-69
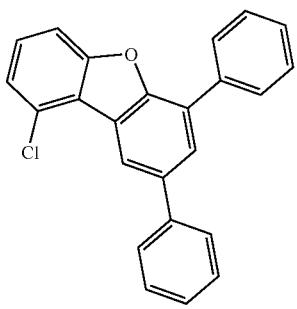
Sub 2-70
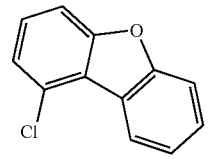
Sub 2-71
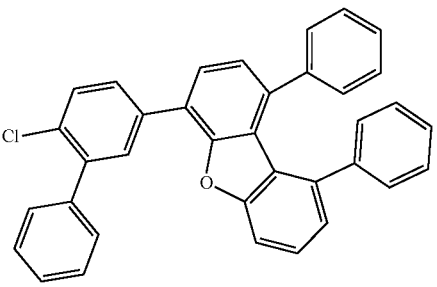
Sub 2-72
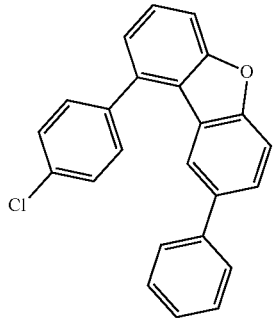
Sub 2-73
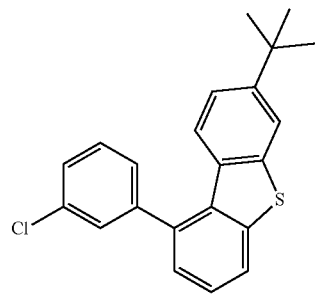

Sub 2-74
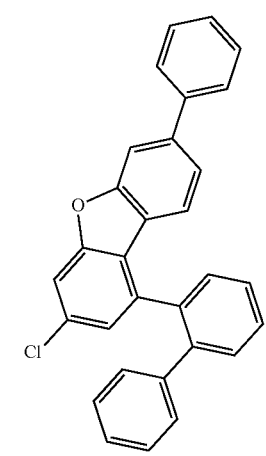
Sub 2-78
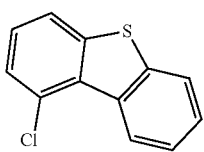
Sub 2-75
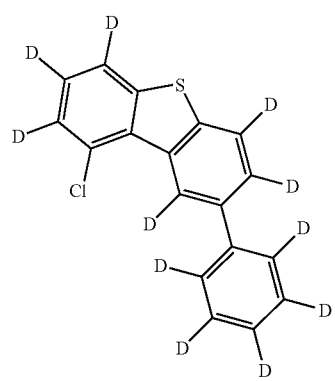
Sub 2-79
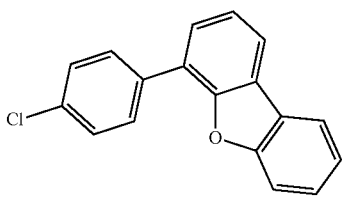
Sub 2-80
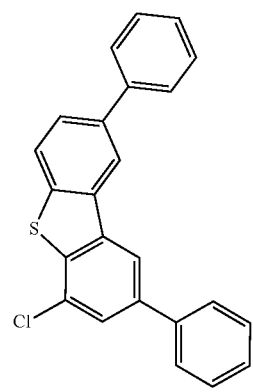
Sub 2-76
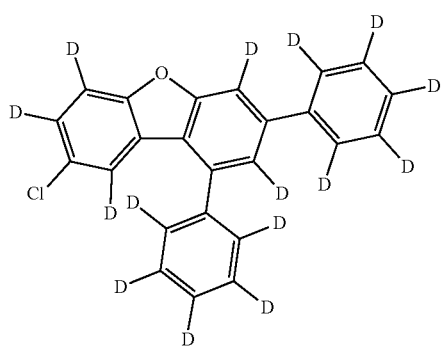
Sub 2-81
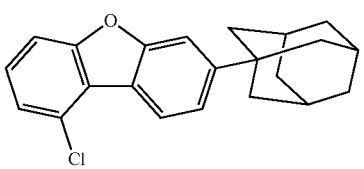
Sub 2-82
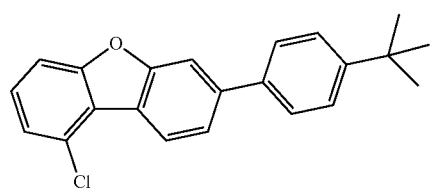
Sub 2-77
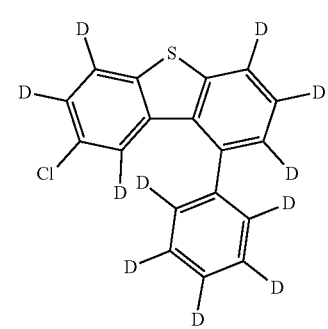
Sub 2-83
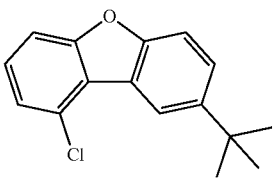
Sub 2-84
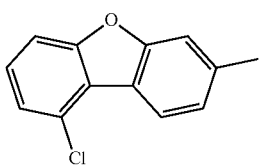

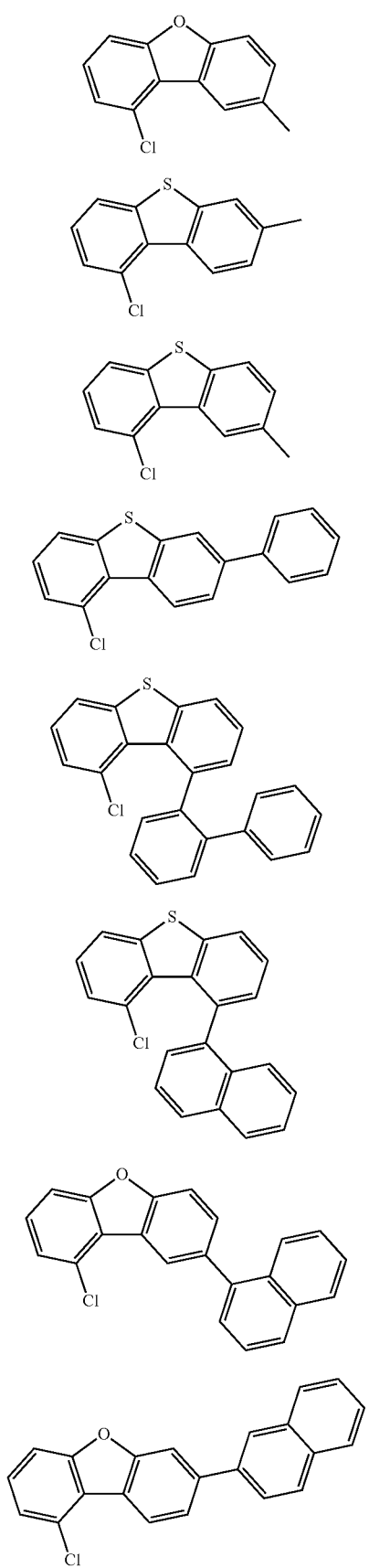
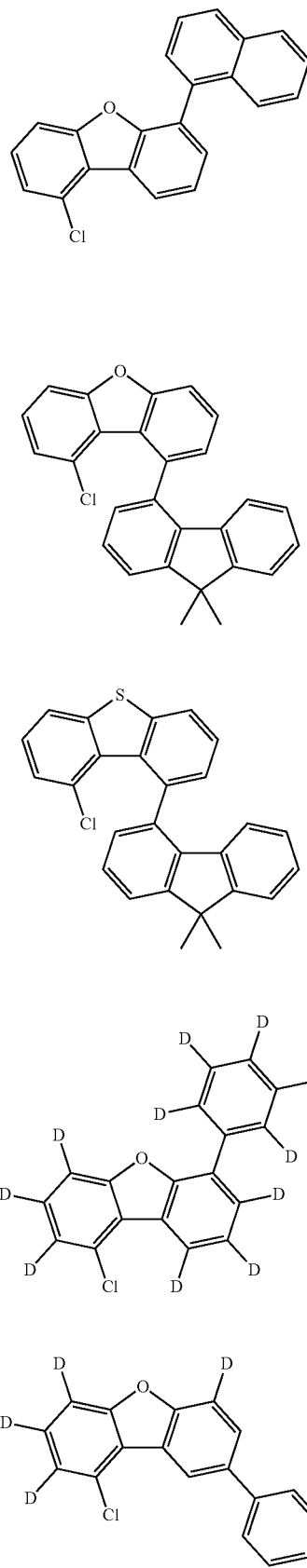
Sub 2-85
Sub 2-86
Sub 2-87
Sub 2-88
Sub 2-89
Sub 2-90
Sub 2-91
Sub 2-92
Sub 2-93
Sub 2-94
Sub 2-95
Sub 2-96
Sub 2-97

TABLE 2

| Compound | FD-MS | Compound | FD-MS |
|---|---|---|---|
| Sub 2-1 | m/z = 278.05($C_{18}H_{11}ClO$ = 278.74) | Sub 2-2 | m/z = 278.05($C_{18}H_{11}ClO$ = 278.74) |
| Sub 2-3 | m/z = 278.05($C_{18}H_{11}ClO$ = 278.74) | Sub 2-4 | m/z = 278.05($C_{18}H_{11}ClO$ = 278.74) |
| Sub 2-5 | m/z = 278.05($C_{18}H_{11}ClO$ = 278.74) | Sub 2-6 | m/z = 278.05($C_{18}H_{11}ClO$ = 278.74) |
| Sub 2-7 | m/z = 278.05($C_{18}H_{11}ClO$ = 278.74) | Sub 2-8 | m/z = 278.05($C_{18}H_{11}ClO$ = 278.74) |
| Sub 2-9 | m/z = 278.05($C_{18}H_{11}ClO$ = 278.74) | Sub 2-10 | m/z = 278.05($C_{18}H_{11}ClO$ = 278.74) |
| Sub 2-11 | m/z = 278.05($C_{18}H_{11}ClO$ = 278.74) | Sub 2-12 | m/z = 278.05($C_{18}H_{11}ClO$ = 278.74) |
| Sub 2-13 | m/z = 278.05($C_{18}H_{11}ClO$ = 278.74) | Sub 2-14 | m/z = 278.05($C_{18}H_{11}ClO$ = 278.74) |
| Sub 2-15 | m/z = 278.05($C_{18}H_{11}ClO$ = 278.74) | Sub 2-16 | m/z = 278.05($C_{18}H_{11}ClO$ = 278.74) |
| Sub 2-17 | m/z = 294.03($C_{18}H_{11}ClS$ = 294.80) | Sub 2-18 | m/z = 294.03($C_{18}H_{11}ClS$ = 294.80) |
| Sub 2-19 | m/z = 294.03($C_{18}H_{11}ClS$ = 294.80) | Sub 2-20 | m/z = 294.03($C_{18}H_{11}ClS$ = 294.80) |
| Sub 2-21 | m/z = 294.03($C_{18}H_{11}ClS$ = 294.80) | Sub 2-22 | m/z = 294.03($C_{18}H_{11}ClS$ = 294.80) |
| Sub 2-23 | m/z = 294.03($C_{18}H_{11}ClS$ = 294.80) | Sub 2-24 | m/z = 294.03($C_{18}H_{11}ClS$ = 294.80) |
| Sub 2-25 | m/z = 294.03($C_{18}H_{11}ClS$ = 294.80) | Sub 2-26 | m/z = 294.03($C_{18}H_{11}ClS$ = 294.80) |
| Sub 2-27 | m/z = 294.03($C_{18}H_{11}ClS$ = 294.80) | Sub 2-28 | m/z = 294.03($C_{18}H_{11}ClS$ = 294.80) |
| Sub 2-29 | m/z = 294.03($C_{18}H_{11}ClS$ = 294.80) | Sub 2-30 | m/z = 294.03($C_{18}H_{11}ClS$ = 294.80) |
| Sub 2-31 | m/z = 294.03($C_{18}H_{11}ClS$ = 294.80) | Sub 2-32 | m/z = 294.03($C_{18}H_{11}ClS$ = 294.80) |
| Sub 2-33 | m/z = 430.11($C_{30}H_{19}ClO$ = 430.93) | Sub 2-34 | m/z = 258.08($C_{16}H_{15}ClO$ = 258.75) |
| Sub 2-35 | m/z = 274.06($C_{16}H_{15}ClS$ = 274.81) | Sub 2-36 | m/z = 294.08($C_{19}H_{15}ClO$ = 294.78) |
| Sub 2-37 | m/z = 354.08($C_{24}H_{15}ClO$ = 354.83) | Sub 2-38 | m/z = 328.07($C_{22}H_{13}ClO$ = 328.80) |
| Sub 2-39 | m/z = 344.04($C_{22}H_{13}ClS$ = 344.86) | Sub 2-40 | m/z = 354.08($C_{24}H_{15}ClO$ = 354.83) |
| Sub 2-41 | m/z = 370.06($C_{24}H_{15}ClS$ = 370.89) | Sub 2-42 | m/z = 496.11($C_{34}H_{21}ClS$ = 497.05) |
| Sub 2-43 | m/z = 504.13($C_{36}H_{21}ClO$ = 505.01) | Sub 2-44 | m/z = 420.07($C_{28}H_{17}ClS$ = 420.95) |
| Sub 2-45 | m/z = 350.09($C_{22}H_{19}ClS$ = 350.90) | Sub 2-46 | m/z = 354.08($C_{24}H_{15}ClO$ = 354.83) |
| Sub 2-47 | m/z = 370.06($C_{24}H_{15}ClS$ = 370.89) | Sub 2-48 | m/z = 344.04($C_{22}H_{13}ClS$ = 344.86) |
| Sub 2-49 | m/z = 328.07($C_{22}H_{13}ClO$ = 328.80) | Sub 2-50 | m/z = 328.07($C_{22}H_{13}ClO$ = 328.80) |
| Sub 2-51 | m/z = 370.06($C_{24}H_{15}ClS$ = 370.89) | Sub 2-52 | m/z = 384.04($C_{24}H_{13}ClOS$ = 384.88) |
| Sub 2-53 | m/z = 292.07($C_{19}H_{13}ClO$ = 292.76) | Sub 2-54 | m/z = 258.08($C_{16}H_{15}ClO$ = 258.75) |
| Sub 2-55 | m/z = 460.07($C_{30}H_{17}ClOS$ = 460.98) | Sub 2-56 | m/z = 334.11($C_{22}H_{19}ClO$ = 334.84) |
| Sub 2-57 | m/z = 258.08($C_{16}H_{15}ClO$ = 258.75) | Sub 2-58 | m/z = 334.11($C_{22}H_{19}ClO$ = 334.84) |
| Sub 2-59 | m/z = 412.16($C_{28}H_{25}ClO$ = 412.96) | Sub 2-60 | m/z = 289.12($C_{18}D_{11}ClO$ = 289.80) |
| Sub 2-61 | m/z = 359.11($C_{24}H_{10}D_5ClO$ = 359.86) | Sub 2-62 | m/z = 202.02($C_{12}H_7ClO$ = 202.64) |
| Sub 2-63 | m/z = 304.07($C_{20}H_{13}ClO$ = 304.77) | Sub 2-64 | m/z = 319.02($C_{19}H_{10}ClNS$ = 319.81) |
| Sub 2-65 | m/z = 354.08($C_{24}H_{15}ClO$ = 354.83) | Sub 2-66 | m/z = 258.08($C_{16}H_{15}ClO$ = 258.75) |
| Sub 2-67 | m/z = 218.00($C_{12}H_7ClS$ = 218.70) | Sub 2-68 | m/z = 354.08($C_{24}H_{15}ClO$ = 354.83) |
| Sub 2-69 | m/z = 354.08($C_{24}H_{15}ClO$ = 354.83) | Sub 2-70 | m/z = 202.02($C_{12}H_7ClO$ = 202.64) |
| Sub 2-71 | m/z = 506.14($C_{36}H_{23}ClO$ = 507.03) | Sub 2-72 | m/z = 354.08($C_{24}H_{15}ClO$ = 354.83) |
| Sub 2-73 | m/z = 350.09($C_{22}H_{19}ClS$ = 350.9) | Sub 2-74 | m/z = 430.11($C_{30}H_{19}ClO$ = 430.93) |
| Sub 2-75 | m/z = 305.10($C_{18}D_{11}ClS$ = 305.86) | Sub 2-76 | m/z = 369.18($C_{24}D_{15}ClO$ = 369.92) |
| Sub 2-77 | m/z = 305.10($C_{18}D_{11}ClS$ = 305.86) | Sub 2-78 | m/z = 218.00($C_{12}H_7ClS$ = 218.70) |
| Sub 2-79 | m/z = 278.05($C_{18}H_{11}ClO$ = 278.74) | Sub 2-80 | m/z = 370.06($C_{24}H_{15}ClO$ = 370.89) |
| Sub 2-81 | m/z = 336.13($C_{22}H_{21}ClO$ = 336.86) | Sub 2-82 | m/z = 334.11 ($C_{22}H_{19}ClO$ = 334.84) |
| Sub 2-83 | m/z = 258.08 ($C_{16}H_{15}ClO$ = 258.75) | Sub 2-84 | m/z = 216.03 ($C_{13}H_9ClO$ = 216.66) |
| Sub 2-85 | m/z = 216.03 ($C_{13}H_9ClO$ = 216.66) | Sub 2-86 | m/z = 232.01 ($C_{13}H_9ClS$ = 232.73) |
| Sub 2-87 | m/z = 232.01 ($C_{13}H_9ClS$ = 232.73) | Sub 2-88 | m/z = 294.03 ($C_{18}H_{11}ClO$ = 294.80) |
| Sub 2-89 | m/z = 370.06 ($C_{24}H_{15}ClS$ = 370.89) | Sub 2-90 | m/z = 328.07 ($C_{22}H_{13}ClO$ = 328.79) |
| Sub 2-91 | m/z = 328.07 ($C_{22}H_{13}ClO$ = 328.79) | Sub 2-92 | m/z = 328.07 ($C_{22}H_{13}ClO$ = 328.79) |
| Sub 2-93 | m/z = 328.07 ($C_{22}H_{13}ClO$ = 328.79) | Sub 2-94 | m/z = 394.11 ($C_{27}H_{19}ClO$ = 394.90) |
| Sub 2-95 | m/z = 410.09 ($C_{27}H_{19}ClS$ = 410.96) | Sub 2-96 | m/z = 289.12 ($C_{18}D_{11}ClO$ = 289.80) |
| Sub 2-97 | m/z = 282.07 ($C_{18}H_7D_4ClO$ = 282.76) | | |

Synthesis Example of Final Product

Synthesis Example of P1-2

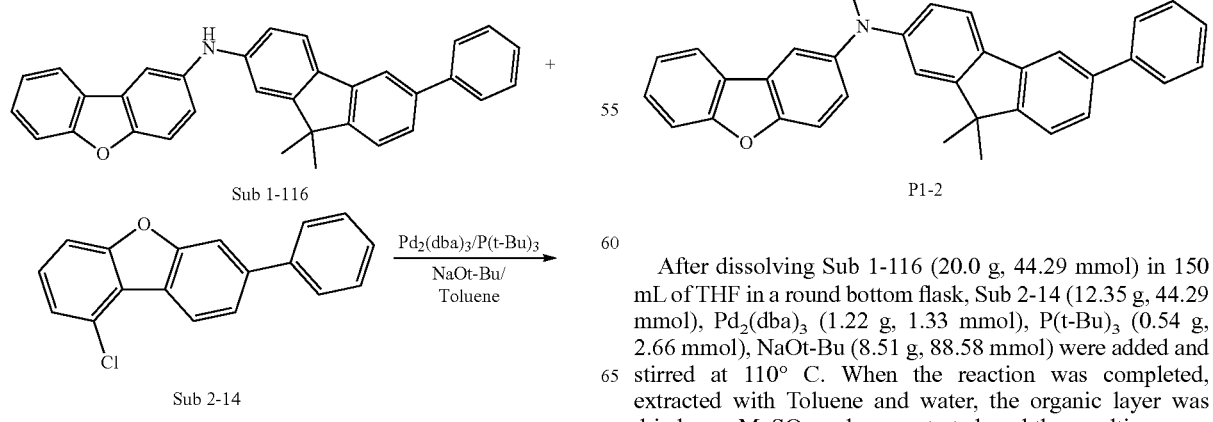

After dissolving Sub 1-116 (20.0 g, 44.29 mmol) in 150 mL of THF in a round bottom flask, Sub 2-14 (12.35 g, 44.29 mmol), $Pd_2(dba)_3$ (1.22 g, 1.33 mmol), $P(t-Bu)_3$ (0.54 g, 2.66 mmol), NaOt-Bu (8.51 g, 88.58 mmol) were added and stirred at 110° C. When the reaction was completed, extracted with Toluene and water, the organic layer was dried over $MgSO_4$ and concentrated, and the resulting compound was recrystallized using a silicagel column to obtain 22.8 g of product (yield: 74%).

SYNTHESIS EXAMPLE OF P1-14

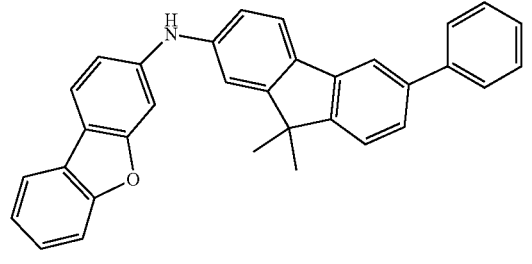

Sub 1-115

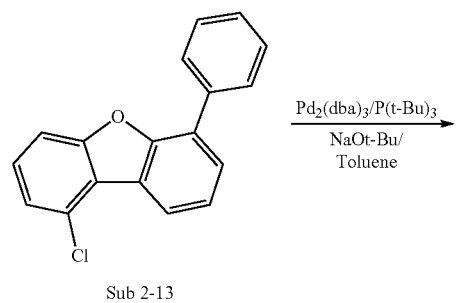

Sub 2-13

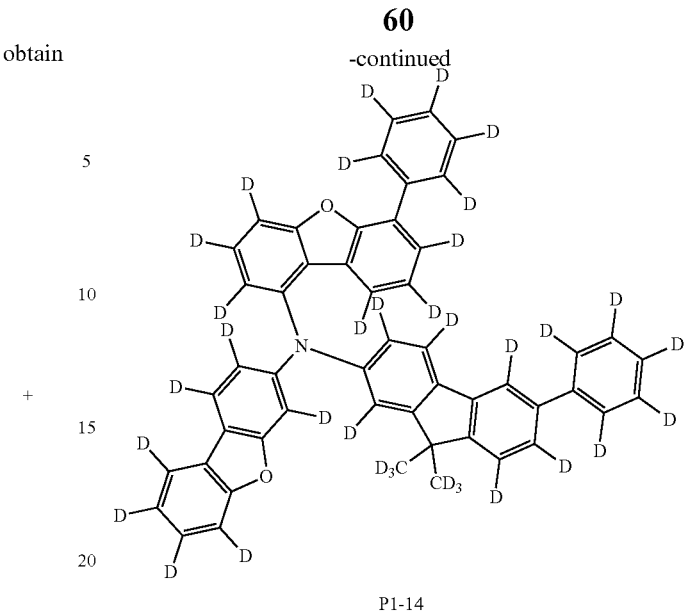

P1-14

(1) Synthesis of P1-14'

After dissolving Sub 1-115 (20.0 g, 44.29 mmol) in toluene (150 mL) in a round bottom flask, Sub 2-13 (12.35 g, 44.29 mmol), $Pd_2(dba)_3$ (1.22 g, 1.33 mmol), $P(t-Bu)_3$ (0.54 g, 2.66 mmol), NaOt-Bu (8.51 g, 88.58 mmol) were added and 23.1 g of product (yield: 75%) was obtained using the synthesis method of P1-2.

(2) Synthesis of P1-14

P1-14' (23.0 g, 33.15 mmol) obtained in the above synthesis was dissolved in Benzene-D6 (680 mL) in a round bottom flask, then $CF_3SO_3H$ (5.86 mL, 66.30 mmol) was slowly added and stirred at room temperature for 16 hours. When the reaction is complete, $Na_2CO_3$ (10.54 g, 99.45 mmol) dissolved in D20 is added to neutralize. After extraction with toluene and D20, the organic layer was dried with $MgSO_4$ and concentrated, and the resulting compound was recrystallized on a silicagel column to obtain 22.5 g of product (yield: 93%).

Synthesis Example of P1-45

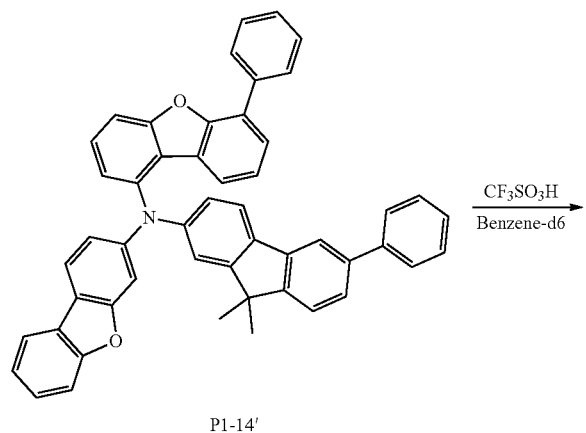

P1-14'

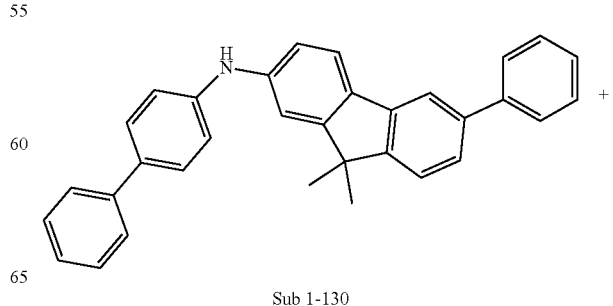

Sub 1-130

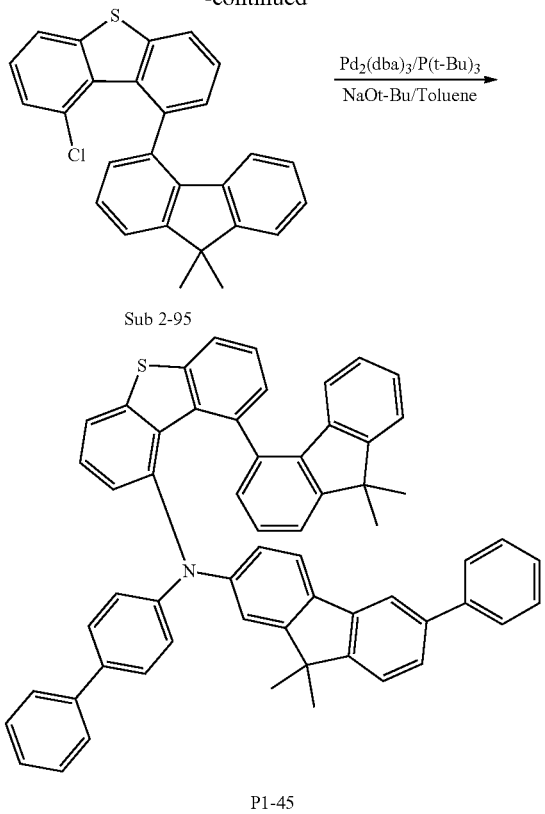

Sub 2-95

P1-45

After dissolving Sub 1-130 (20.0 g, 45.70 mmol) in toluene (150 mL) in a round bottom flask, Sub 2-95 (18.78 g, 45.70 mmol), Pd$_2$(dba)$_3$ (1.26 g, 1.37 mmol), P(t-Bu)$_3$ (0.56 g, 2.74 mmol), NaOt-Bu (8.79 g, 91.41 mmol) were added and 26.8 g of product (yield: 72%) was obtained using the synthesis method of P1-2.

In the above, exemplary synthesis examples of the present invention represented by Formula (1) have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh$_3$-mediated reductive cyclization reaction (*J. Org. Chem.* 2005, 70, 5014.), and it will be easily understood by those skilled in the art that the reaction proceeds even when other substituents defined in Formula (1) are bonded in addition to the substituents specified in the specific synthesis examples.

EXAMPLE 1

Green Organic Light Emitting Device
(Emitting-Auxiliary Layer)

Compound A and Compound B were used on the ITO layer (anode) formed on the glass substrate, and a hole injection layer with a thickness of 10 nm was formed by doping Compound B at a weight ratio of 98:2, and Compound A was vacuum deposited to a thickness of 110 nm on the hole injection layer to form a hole transport layer. Next, compound P1-1 of the present invention was vacuum deposited to a thickness of 10 nm on the hole transport layer to form an emitting-auxiliary layer. Afterwards, compound D-G was used as the host material of the emitting layer and tris(2-phenylpyridine)-iridium (hereinafter, 'Ir(ppy)$_3$') was used as the dopant material, and the dopants were doped in a 90:10 weight ratio to form an emitting layer with a thickness of 30 nm.

Next, Compound E is vacuum deposited on the emitting layer to form a hole blocking layer with a thickness of 10 nm, and an electron transport layer with a thickness of 30 nm was formed on the hole blocking layer using a mixture of Compound F and Compound G at a weight ratio of 5:5. Afterwards, Compound G was deposited on the electron

TABLE 3

| Compound | FD-MS | Compound | FD-MS |
|---|---|---|---|
| P1-1 | m/z = 693.27 (C$_{51}$H$_{35}$NO$_2$ = 693.85) | P1-2 | m/z = 693.27 (C$_{51}$H$_{35}$NO$_2$ = 693.85) |
| P1-3 | m/z = 693.27 (C$_{51}$H$_{35}$NO$_2$ = 693.85) | P1-4 | m/z = 719.32 (C$_{54}$H$_{41}$NO = 719.93) |
| P1-5 | m/z = 693.27 (C$_{51}$H$_{35}$NO$_2$ = 693.85) | P1-6 | m/z = 693.27 (C$_{51}$H$_{35}$NO$_2$ = 693.85) |
| P1-7 | m/z = 693.27 (C$_{51}$H$_{35}$NO$_2$ = 693.85) | P1-8 | m/z = 679.29 (C$_{51}$H$_{37}$NO = 679.86) |
| P1-9 | m/z = 603.26 (C$_{45}$H$_{33}$NO$_2$ = 603.76) | P1-10 | m/z = 603.26 (C$_{45}$H$_{33}$NO$_2$ = 603.76) |
| P1-11 | m/z = 735.35 (C$_{55}$H$_{45}$NO = 735.97) | P1-12 | m/z = 701.31 (C$_{51}$H$_{43}$NS = 701.97) |
| P1-13 | m/z = 597.30 (C$_{44}$H$_{39}$NO = 597.80) | P1-14 | m/z = 728.49 (C$_{51}$D$_{35}$NO$_2$ = 729.06) |
| P1-15 | m/z = 621.30 (C$_{46}$H$_{39}$NO = 621.82) | P1-16 | m/z = 639.30 (C$_{46}$H$_{41}$NS = 639.90) |
| P1-17 | m/z = 728.49 (C$_{51}$D$_{35}$NO$_2$ = 729.06) | P1-18 | m/z = 704.34 (C$_{51}$H$_{24}$D$_{11}$NO$_2$ = 704.91) |
| P1-19 | m/z = 673.30 (C$_{49}$D$_{39}$NO$_2$ = 673.86) | P1-20 | m/z = 673.30 (C$_{49}$D$_{39}$NO$_2$ = 673.86) |
| P1-21 | m/z = 843.35 (C$_{64}$H$_{45}$NO = 844.07) | P1-22 | m/z = 843.35 (C$_{64}$H$_{45}$NO = 844.07) |
| P1-23 | m/z = 843.35 (C$_{64}$H$_{45}$NO = 844.07) | P1-24 | m/z = 719.32 (C$_{54}$H$_{41}$NO = 719.93) |
| P1-25 | m/z = 719.32 (C$_{54}$H$_{41}$NO = 719.93) | P1-26 | m/z = 805.33 (C$_{61}$H$_{43}$NO = 806.02) |
| P1-27 | m/z = 779.32 (C$_{59}$H$_{41}$NO = 799.98) | P1-28 | m/z = 771.30 (C$_{57}$H$_{41}$NS = 772.02) |
| P1-29 | m/z = 631.25 (C$_{46}$H$_{33}$NO$_2$ = 631.77) | P1-30 | m/z = 631.25 (C$_{46}$H$_{33}$NO$_2$ = 631.77) |
| P1-31 | m/z = 647.23 (C$_{46}$H$_{33}$NOS = 647.84) | P1-32 | m/z = 647.23 (C$_{46}$H$_{33}$NOS = 647.84) |
| P1-33 | m/z = 743.28 (C$_{55}$H$_{37}$NO$_2$ = 743.91) | P1-34 | m/z = 743.28 (C$_{55}$H$_{37}$NO$_2$ = 743.91) |
| P1-35 | m/z = 749.33 (C$_{55}$H$_{43}$NO$_2$ = 749.95) | P1-36 | m/z = 769.33 (C$_{58}$H$_{43}$NO = 769.99) |
| P1-37 | m/z = 769.30 (C$_{57}$H$_{39}$NO$_2$ = 769.94) | P1-38 | m/z = 785.28 (C$_{57}$H$_{39}$NOS = 786.00) |
| P1-39 | m/z = 769.30 (C$_{57}$H$_{39}$NO$_2$ = 769.94) | P1-40 | m/z = 785.28 (C$_{57}$H$_{39}$NOS = 786.00) |
| P1-41 | m/z = 683.31 (C$_{51}$H$_{33}$D$_4$NO = 683.89) | P1-42 | m/z = 527.22 (C$_{39}$H$_{29}$NO = 527.67) |
| P1-43 | m/z = 769.30 (C$_{57}$H$_{39}$NO$_2$ = 769.94) | P1-44 | m/z = 801.25 (C$_{57}$H$_{39}$NS$_2$ = 802.07) |
| P1-45 | m/z = 811.33 (C$_{60}$H$_{45}$NS = 812.09) | P1-46 | m/z = 871.38 (C$_{66}$H$_{49}$NO = 872.12) |
| P1-47 | m/z = 795.35 (C$_{60}$H$_{45}$NO = 796.03) | P1-48 | m/z = 811.33 (C$_{60}$H$_{45}$NS = 812.09) |
| P1-49 | m/z = 819.30 (C$_{61}$H$_{41}$NS = 820.07) | P1-50 | m/z = 643.29 (C$_{48}$H$_{37}$NO = 643.83) |
| P1-51 | m/z = 709.24 (C$_{51}$H$_{35}$NOS = 709.91) | | | transport layer to form an electron injection layer with a thickness of 0.2 nm, and then Al was deposited to form a cathode with a thickness of 150 nm.

- compound A: N-([1,1'-biphenyl]-4-yl)-9,9-dimethyl-N-(4-(9-phenyl-9H-carbazol-3-yl)phenyl)-9H-fluoren-2-amine
- compound B: 4,4',4"-((1E,1'E,1"E)-cyclopropane-1,2,3-triylidenetris(cyanomethaneylylidene))tris(2,3,5,6-tetrafluorobenzonitrile)
- compound D-G: 5-(3-(4,6-diphenyl-1,3,5-triazin-2-yl)phenyl)-7,7-dimethyl-5,7-dihydroindeno[2,1-b]carbazole
- compound E: 2-(4'-(9,9-dimethyl-9H-fluoren-2-yl)-[1,1'-biphenyl]-3-yl)-4,6-diphenyl-1,3,5-triazine
- compound F: 2,7-bis(4-(4,6-diphenyl-1,3,5-triazin-2-yl)phenyl)naphthalene
- compound G: (8-quinolinolato)lithium EXAMPLE 2 to EXAMPLE 14

An organic light emitting device was manufactured in the same manner as in Example 1, except that the compound of the present invention shown in Table 4 was used as the emitting-auxiliary layer material instead of the compound P1-1 of the present invention.

COMPARATIVE EXAMPLE 1 TO COMPARATIVE EXAMPLE 4

An organic electroluminescent device was manufactured in the same manner as in Example 1, except that Comparative Compounds E to Comparative Compound H were used instead of Compound P1-1 of the present invention as the emitting-auxiliary layer material.

[comparative compound E]

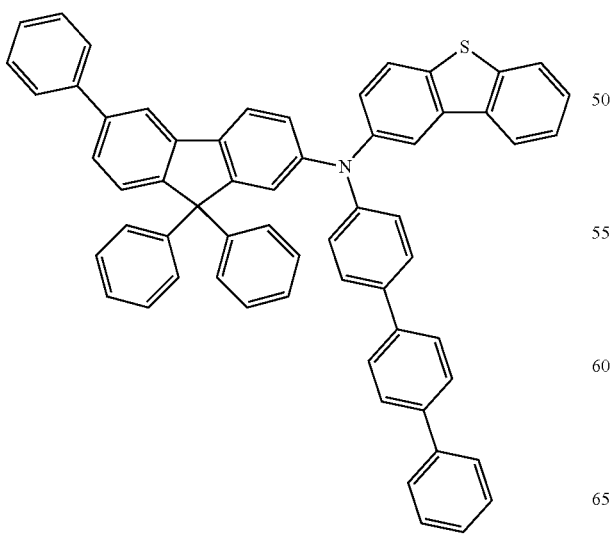

[comparative compound F]

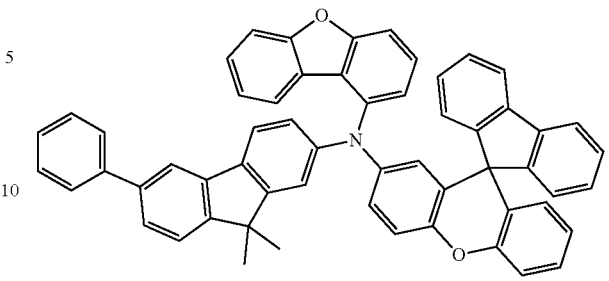

[comparative compound G]

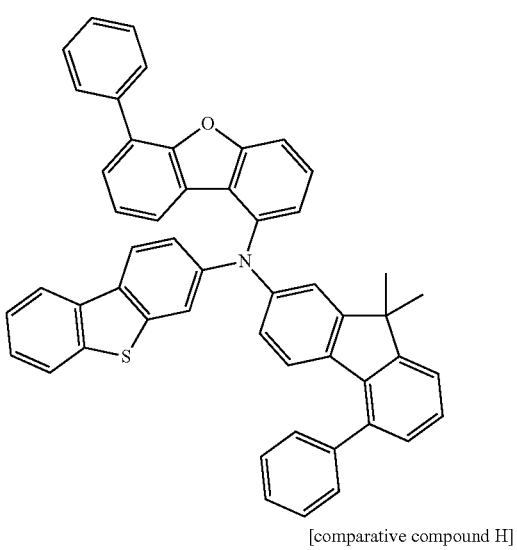

[comparative compound H]

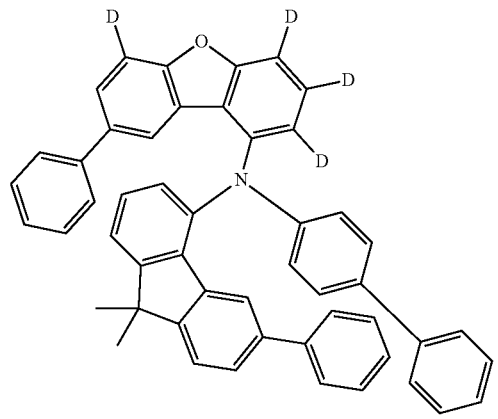

A forward bias direct current voltage was applied to the organic electroluminescent devices of Examples and Comparative Examples manufactured in this way, and the electroluminescence (EL) characteristics were measured using PR-650 from Photoresearch. As a result of the measurement, T95 life was measured at a standard luminance of 5000 cd/m$^2$ through life measuring apparatus manufactured by McScience. Table 4 shows the results of device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 4

|  | compound | Voltage | Current Density (mA/cm$^2$) | Efficiency (cd/A) | T(95) |
|---|---|---|---|---|---|
| comparative example(1) | comparative compound E | 4.8 | 11.0 | 45.4 | 83.4 |
| comparative example(2) | comparative compound F | 5.4 | 12.4 | 40.3 | 94.6 |
| comparative example(3) | comparative compound G | 5.2 | 11.5 | 43.3 | 92.7 |
| comparative example(4) | comparative compound H | 5.3 | 12.0 | 41.7 | 98.6 |
| example(1) | compound(P1-1) | 4.4 | 9.3 | 53.6 | 121.4 |
| example(2) | compound(P1-3) | 4.5 | 9.2 | 54.2 | 122.9 |
| example(3) | compound(P1-5) | 4.5 | 9.6 | 52.3 | 124.4 |
| example(4) | compound(P1-6) | 4.5 | 9.7 | 51.6 | 128.3 |
| example(5) | compound(P1-9) | 4.4 | 9.5 | 52.7 | 121.0 |
| example(6) | compound(P1-14) | 4.5 | 9.2 | 54.1 | 125.6 |
| example(7) | compound(P1-20) | 4.4 | 9.4 | 53.2 | 122.1 |
| example(8) | compound(P1-21) | 4.5 | 9.8 | 51.1 | 120.1 |
| example(9) | compound(P1-37) | 4.5 | 9.5 | 52.5 | 127.0 |
| example(10) | compound(P1-41) | 4.4 | 9.5 | 52.6 | 123.6 |
| example(11) | compound(P1-42) | 4.4 | 9.3 | 53.6 | 116.1 |
| example(12) | compound(P1-49) | 4.5 | 9.3 | 53.7 | 116.8 |
| example(13) | compound(P1-50) | 4.3 | 9.1 | 55.2 | 111.4 |
| example(14) | compound(P1-51) | 4.5 | 9.2 | 54.2 | 122.9 |

As can be seen from the results in Table 4, when a green organic electroluminescent device is manufactured using the material for an organic electroluminescent device of the present invention as a material for the emitting auxiliary layer, the compounds of the present invention exhibit remarkable properties in device performance compared to the comparative example using Comparative Compound E to Comparative Compound H.

As can be seen above, comparing Comparative Compound E and the compound of the present invention, the compound of the present invention is dibenzofuran or dibenzothiophene with an amino group bonded to position 1, while comparative compound E is dibenzothiophene with an amino group bonded to position 2.

In other words, there is a difference in that the bonding position of dibenzofuran or dibenzothiophene is different. The differences can be confirmed through Table 5.

Table 5 shows data measured for Comparative Compound E and Compound P1-49 of the present invention using the DFT Method (B3LYP/6-31g(D)) of the Gaussian program.

TABLE 5

|  | Comparative compound E | P1-49 |
|---|---|---|
| HOMO (eV) | −4.84 | −4.96 |
| LUMO (eV) | −1.13 | −1.19 |
| T1 (eV) | 2.60 | 2.67 |

If Table 5 is described in detail, P1-49, the compound of the present invention, has a deeper HOMO value and higher T1 than the comparative compound E. That is, the hole injection characteristics moving to the host are excellent due to the deep HOMO, which results in increased efficiency. In other words, hole injection into the host is accelerated, resulting in increased efficiency. Specifically, in the case of No. 1 dibenzofuran or dibenzothiophene, it can be seen that the lifespan is excellent, and this appears to be an effect that occurs as T1 increases.

Second, comparing comparative compound F and the compound of the present invention, Comparative compound F has the xanthene structure bonded within the structure, whereas the compound of the present invention differs in that an aryl group, fluorenyl group, dibenzofuran, or dibenzothiophene is bonded instead of Xanthene. Also, when comparing Comparative Compound G and the compound of the present invention, Comparative compound G has a substituent bonded to the 5th position of fluorene, whereas the compound of the present invention differs in that a substituent is bonded to the 6th position of fluorene. Finally, when comparing comparative compound H and the compound of the present invention, Comparative compound H has an amino group bonded to the 4th position of fluorene, whereas the compound of the present invention has a difference in that an amino group is bonded to the 2nd position of fluorene. Regarding this, we attempted to confirm the difference through Table 6.

Table 6 describes the calculated Reorganization Energy values of Comparative Compound F to Comparative Compound H, P1-41, P1-50, and P1-51.

The RE values shown in Table 6 mean the calculated REhole values.

TABLE 6

|  | Reorganization Energy (eV) |
|---|---|
| Comparative compound F | 0.199 |
| Comparative compound G | 0.176 |
| Comparative compound H | 0.186 |
| P1-41 | 0.167 |
| P1-50 | 0.154 |
| P1-51 | 0.168 |

According to Table 6, it can be seen that the compound of the present invention has a lower RE value compared to Comparative Compound F to Comparative Compound H. This means that the compound of the present invention can be seen to have higher hole transfer characteristics compared to Comparative Compound F to Comparative Compound H, and as a result, it is believed to exhibit high efficiency at the same time as fast driving voltage. That is, the combination of specific substituents substituted for amines shows a positive effect on the overall charge mobility, which appears to show a significantly improved overall result. Therefore, it can be confirmed that even within the same skeleton, the characteristics are very different depending on the type of substituent and the position of substitution.

That is, as can be seen from the results of Tables 4 to 6, it can be confirmed that the compound satisfying all the structural characteristics and composition disclosed in the present invention shows a remarkable effect in organic electronic elements compared to comparative compounds having a structurally similar composition with the compound of the present invention, and this shows that the compound of the present invention, which satisfies all specific compositions, exhibits a remarkable effect compared to other comparative compounds not described in this specification.

These results show that even in compounds with similar molecular components, depending on the type and substitution position of the substituent being substituted, the properties of compounds such as the hole characteristics, light efficiency characteristics, energy level, hole injection and mobility characteristics, charge balance of holes and electrons, volume density, and intermolecular distance of the molecule may vary significantly enough to be difficult to predict, and that also, the composition of one compound does not affect the results of the entire element, but the performance of the element can vary depending on complex factors.

In the case of an emitting-auxiliary layer, since the interrelationship between the hole transport layer and the emitting layer (host) must be understood, and even if a similar core is used, it would be very difficult for a person skilled in the art to infer the characteristics shown by the emitting-auxiliary layer using the compound of the present invention.

In addition, in the above-described the evaluation results of element fabrication, the element characteristics were explained by applying the compound of the present invention only to the emitting-auxiliary layer, but the compound of the present invention can be used by applying it to the hole transport layer or to both the hole transport layer and the emitting-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:
1. A compound represented by Formula (1):

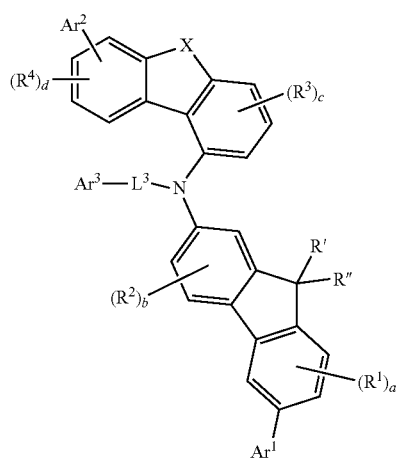

Formula (1)

wherein:
$R^1$, $R^2$, $R^3$ and $R^4$ being the same or different from each other, are each independently selected from the group consisting of hydrogen; deuterium; a halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

a, b, c and d are each independently an integer of 0 to 3,
R', R" and $Ar^1$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and R' and R" may be bonded to each other to form a ring, with the proviso that: $Ar^1$ does not form a ring with an adjacent group, and a N-containing heterocyclic group is excluded from $Ar^1$,
X is O or S,
$L^3$ is selected from the group consisting of a single bond; a $C_6$-$C_{60}$ arylene group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;
$Ar^2$ is selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;
$Ar^3$ is a $C_6$-$C_{60}$ aryl group; a fluorenyl group; or a substituent represented by any of Formulas Ar-1 to Ar-6:

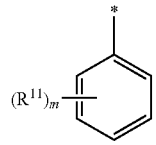

<Formula Ar-1>

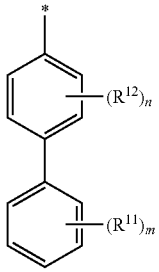

<Formula Ar-2>

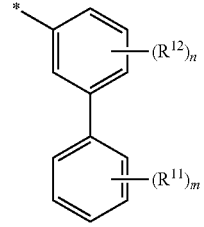

<Formula Ar-3>

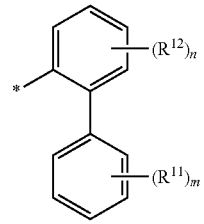

<Formula Ar-4>

-continued

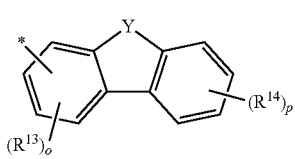
<Formula Ar-5>

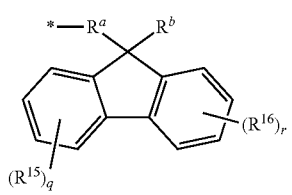
<Formula Ar-6> wherein:
$R^{11}$, $R^{12}$, $R^{13}$, $R^{14}$, $R^{15}$ and $R^{16}$ are the same as the definition of $R^1$,
m is an integer of 0 to 5, n, p, q and r are each independently an integer of 0 to 4, o is an integer of 0 to 3,
Y is O, S, $CR^xR^y$ or $NR^z$,
$R^a$ is a divalent group of the definition of R'; $R^b$, $R^x$, $R^y$ and $R^z$ are the same as the definition of R'; and $R^a$ and $R^b$, or $R^x$ and $R^y$ may be bonded to each other to form a ring,
* refers to the position where $L^3$ is to be bonded,
wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; a halogen; a silane group; a siloxane group; a boron group; a germanium group; a cyano group; a nitro group; a $C_1$-$C_{20}$ alkylthio group; a a$C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group; and the hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein $Ar^3$ is the substituent represented by any one of Formulas Ar-1 to Ar-6.

3. The compound of claim 1, wherein $L^3$ is represented by any one of Formulas L-1 to L-3:

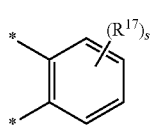
<Formula L-1>

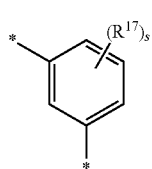
<Formula L-2>

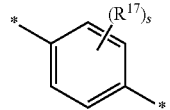
<Formula L-3> wherein:
$R^{17}$ is the same as the definition of $R^1$,
s is an integer of 0 to 4, and
* means a position to be bonded.

4. The compound of claim 1, wherein the compound represented by Formula (1) is any one of the following compounds P1-1 to P1-51:

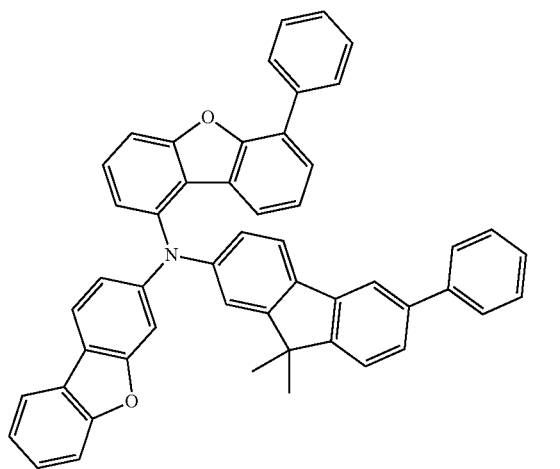

P1-1

P1-2

P1-3

P1-4
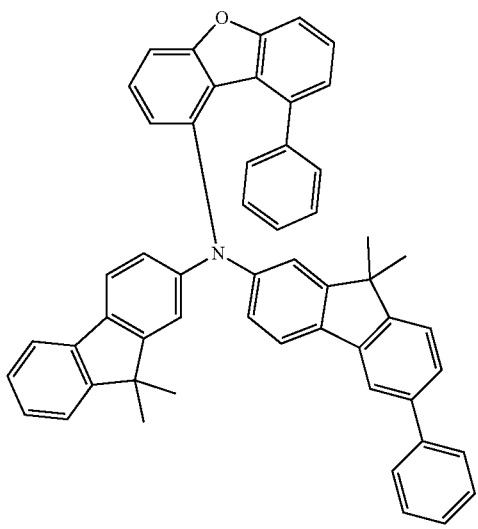
P1-5
P1-6
P1-7
P1-8
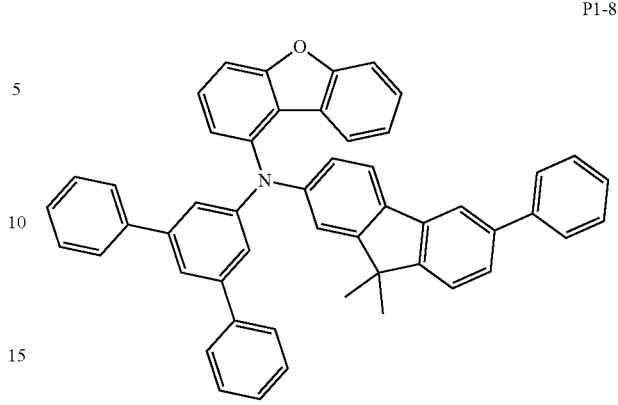
P1-9
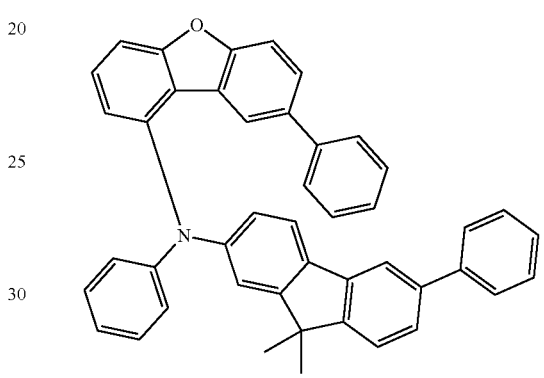
P1-10
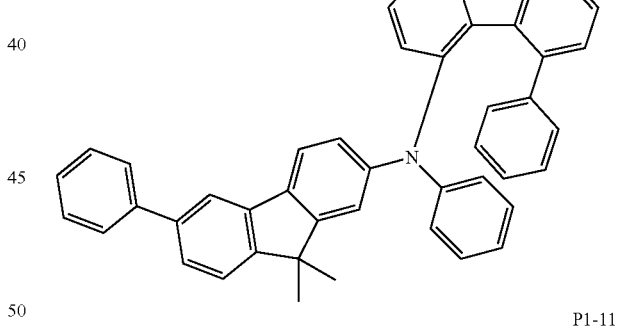
P1-11
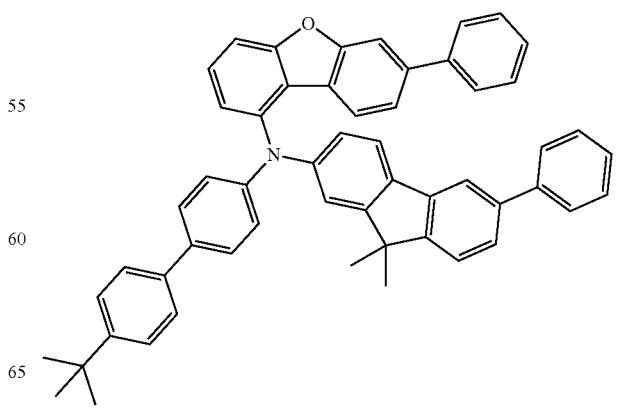

P1-12
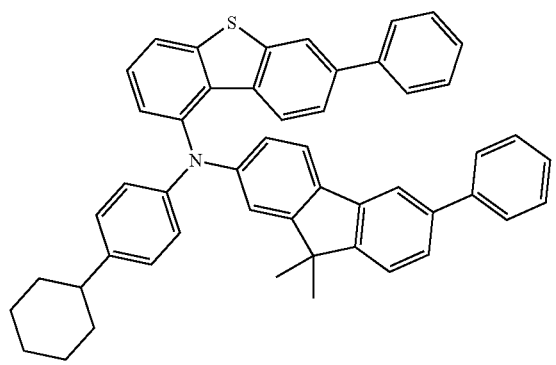
P1-15
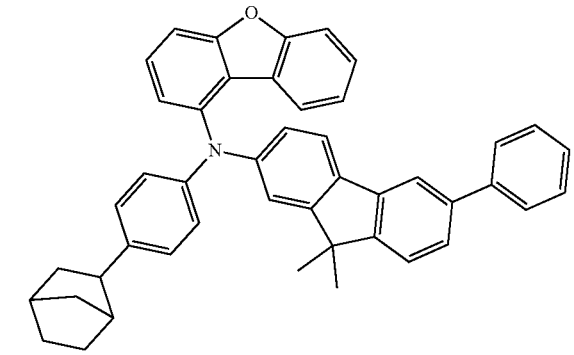
P1-13
P1-16
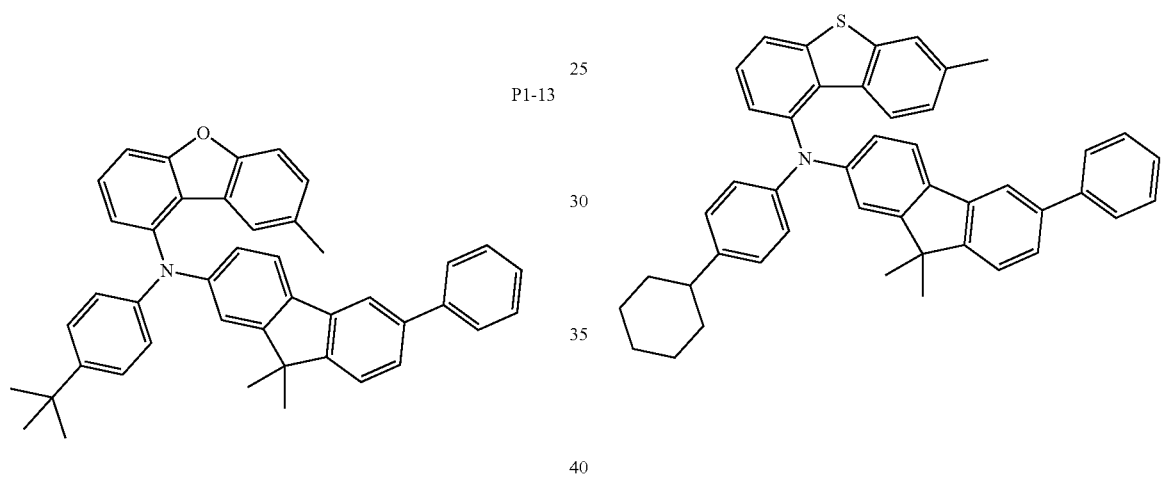
P1-14
P1-17
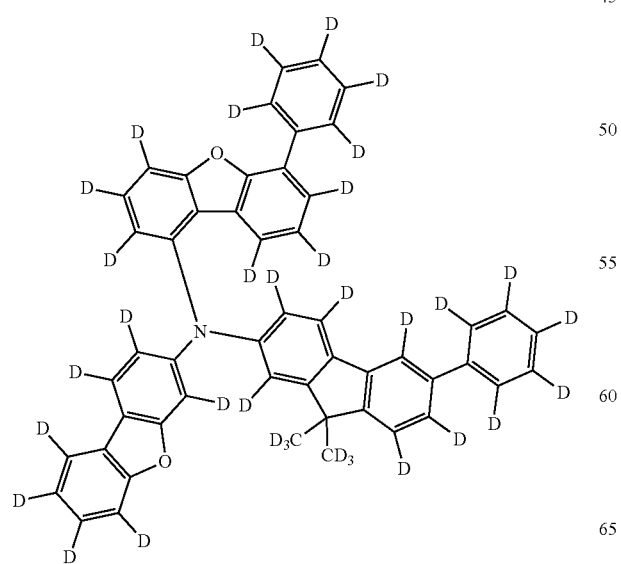
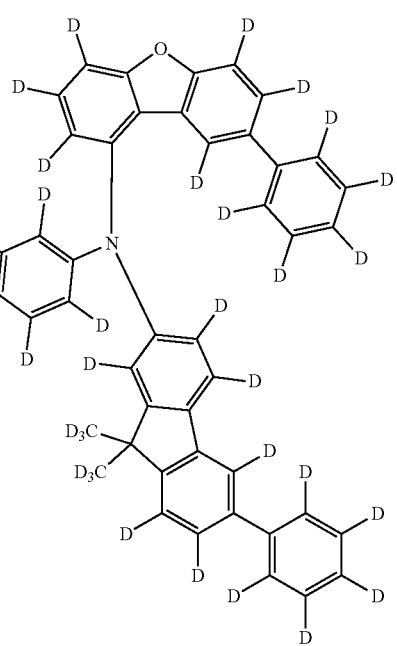

-continued
P1-18
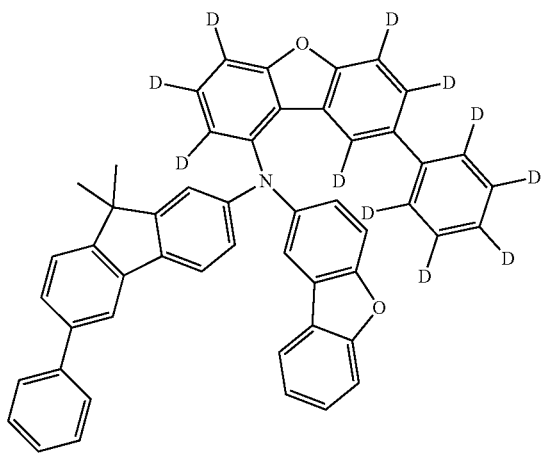
P1-19
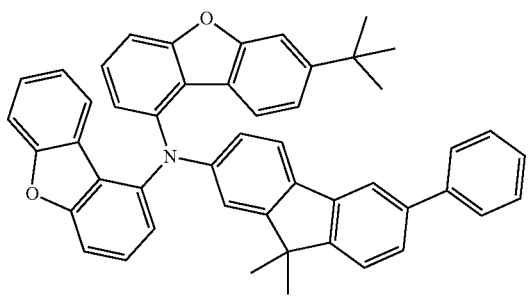
P1-20
P1-21
P1-22
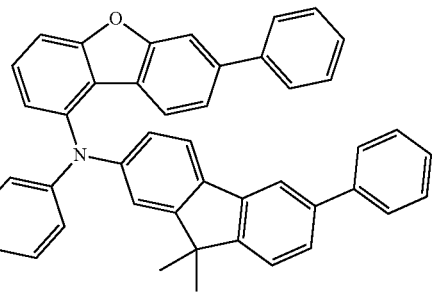
P1-23
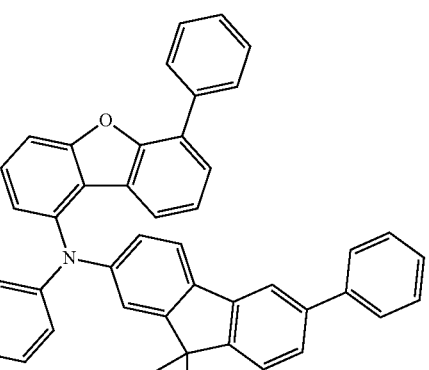
P1-24
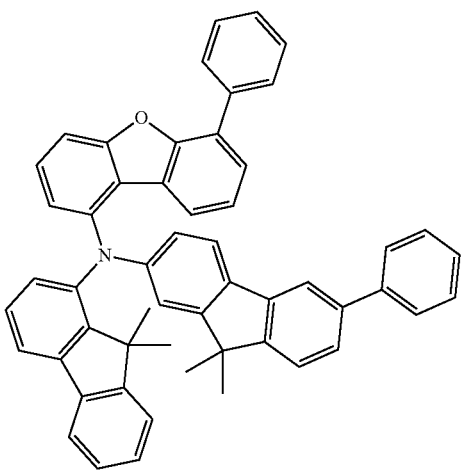

P1-25
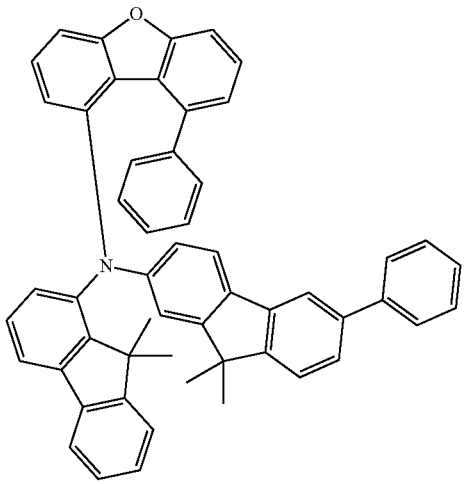
P1-28
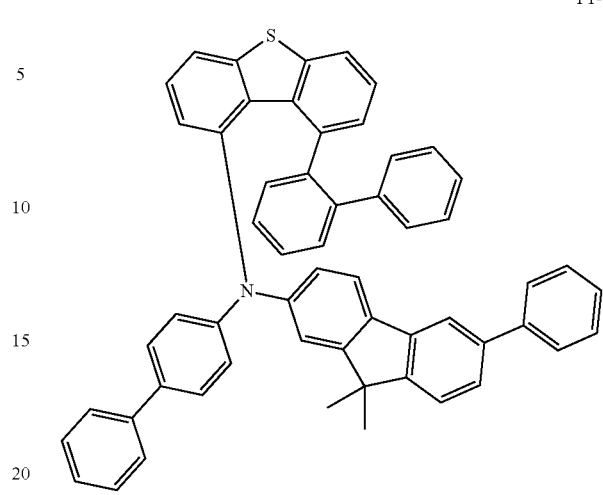
P1-26
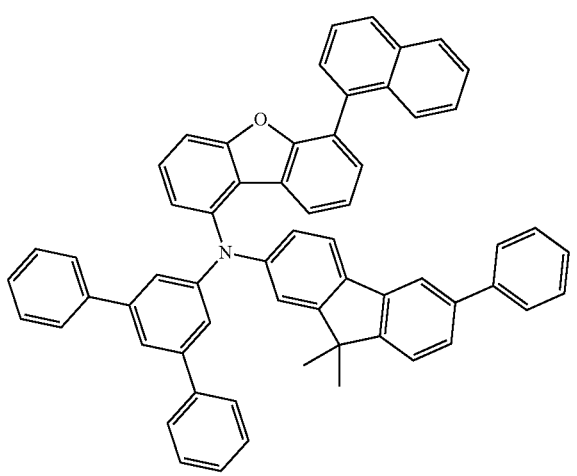
P1-29
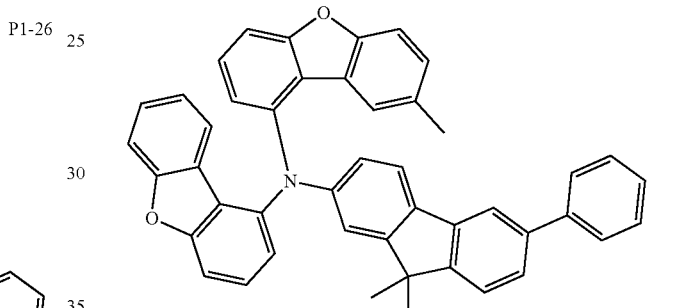
P1-30
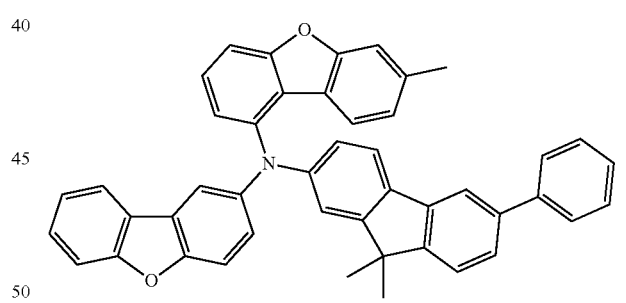
P1-27
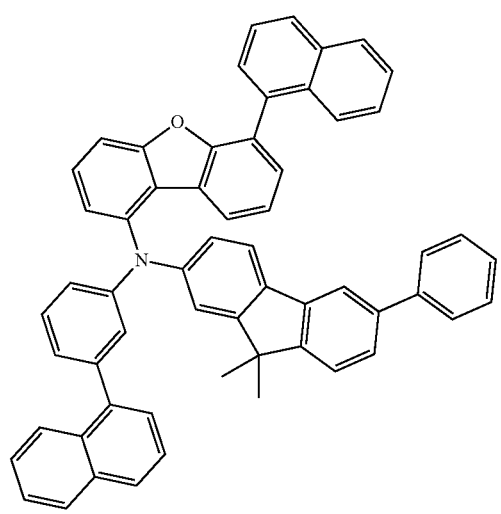
P1-31
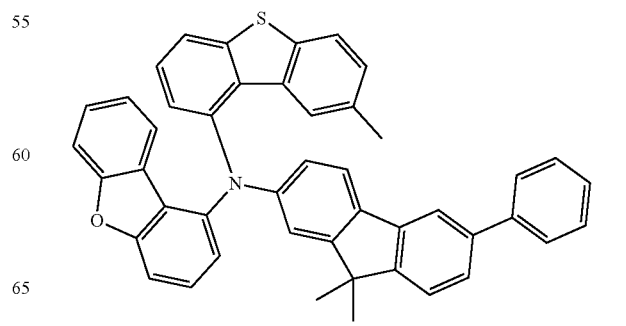

P1-32
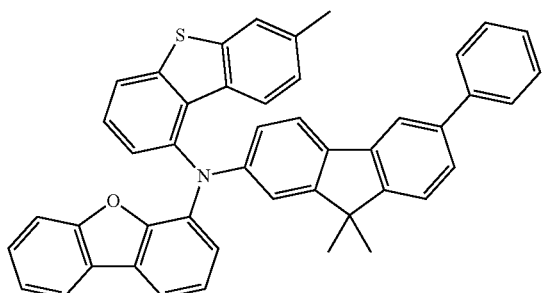
P1-33
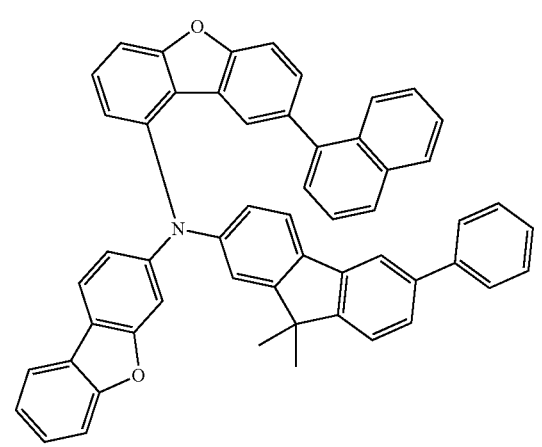
P1-34
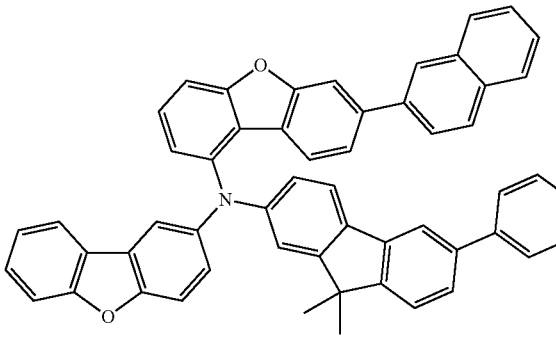
P1-35
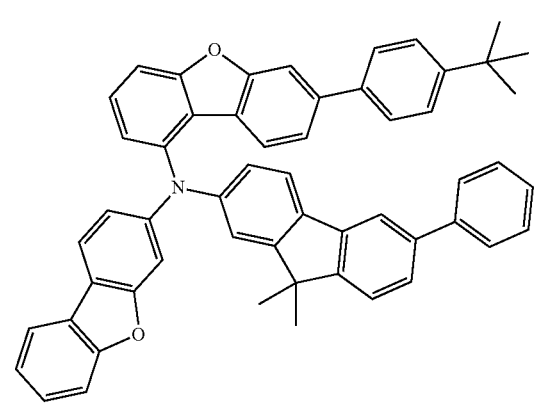
P1-36
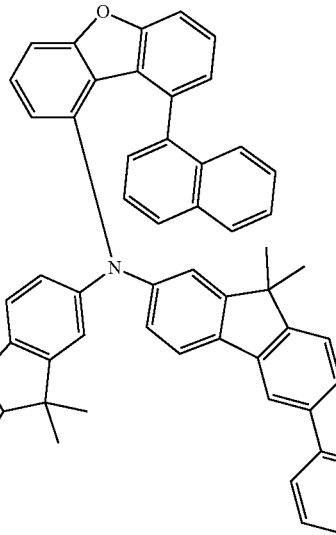
P1-37
P1-38
P1-39

P1-40
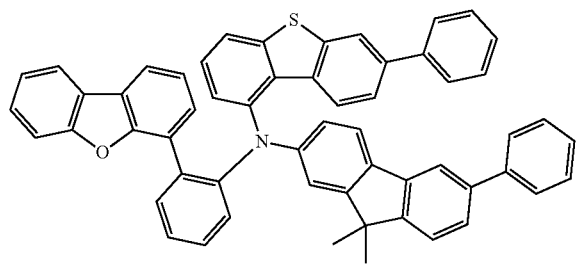
P1-41
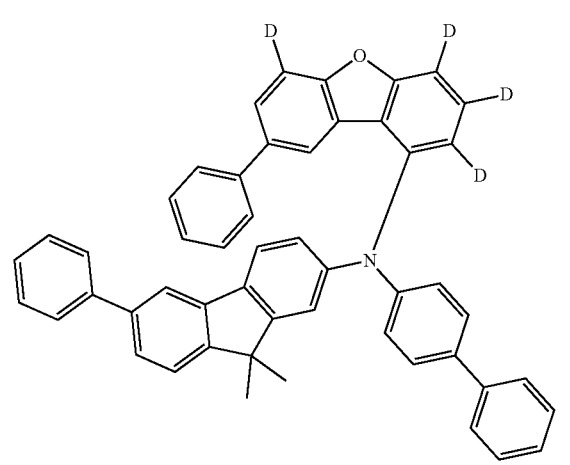
P1-42
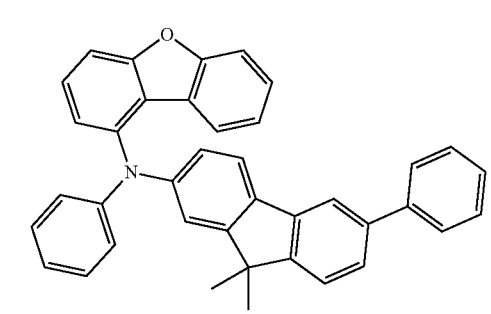
P1-43
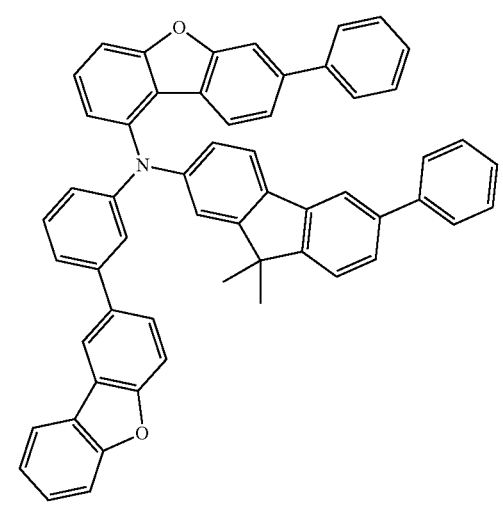
P1-44
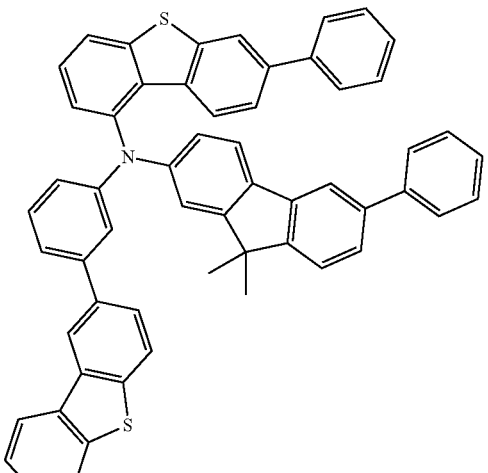
P1-45
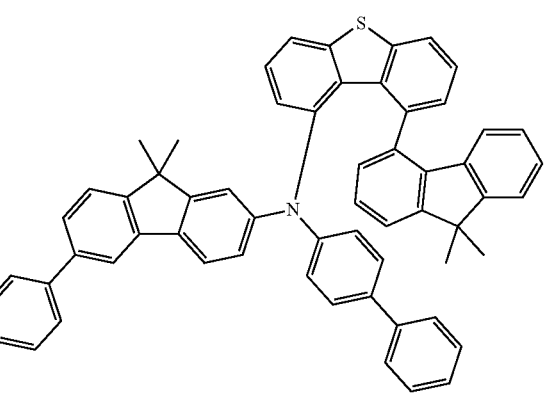
P1-46
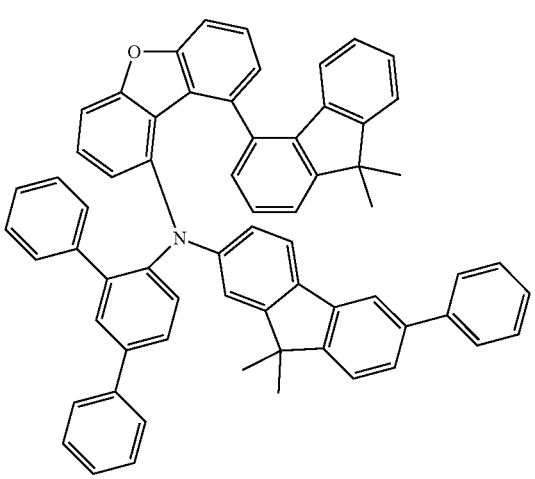

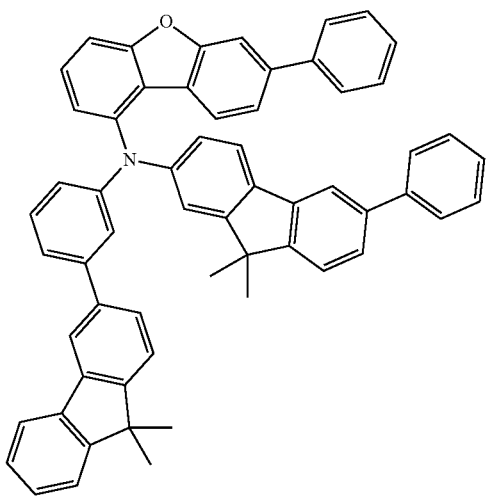

P1-47

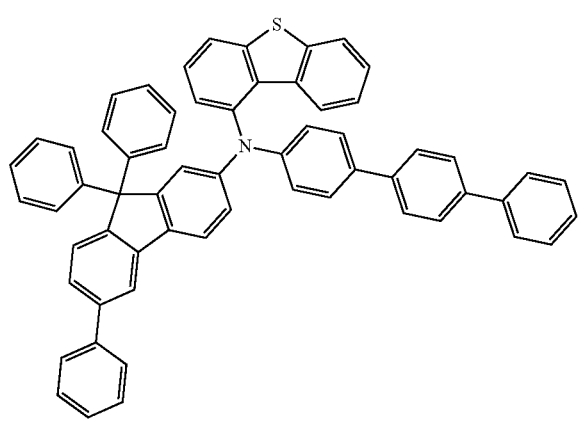

P1-48

P1-49

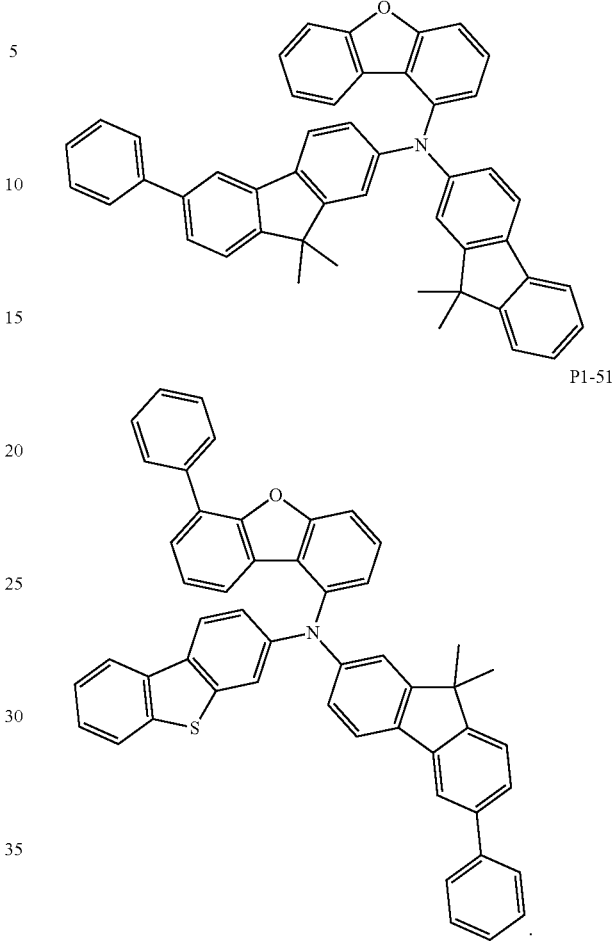

P1-50

P1-51

5. An organic electronic element comprising an anode; a cathode; and an organic material layer between the anode and the cathode, wherein the organic material layer comprises a single compound or 2 or more compounds represented by Formula (1) of claim 1.

6. The organic electronic element of claim 5, wherein the organic material layer comprises at least one of a hole injection layer, a hole transport layer, an emitting-auxiliary layer, an emitting layer, an electron transport auxiliary layer, an electron transport layer and an electron injection layer.

7. The organic electronic element of claim 5, wherein the organic material layer is an emitting-auxiliary layer.

8. The organic electronic element of claim 5, further comprising a light efficiency enhancing layer formed on at least one surface of the anode and the cathode, the surface being opposite to the organic material layer.

9. The organic electronic element of claim 5, wherein the organic material layer comprises 2 or more stacks comprising a hole transport layer, an emitting layer and an electron transport layer sequentially formed on the anode.

10. The organic electronic element of claim 9, wherein the organic material layer further comprises a charge generation layer formed between the 2 or more stacks.

11. An electronic device comprising a display device comprising the organic electronic element of claim 5; and a control unit for driving the display device.

12. The electronic device according to claim 11, wherein the organic electronic element is at least one of an OLED, an organic solar cell, an organic photo conductor (OPC), organic transistor (organic TFT) and an element for monochromic or white illumination.

13. A method for reusing a compound of Formula (1) of claim 1 comprising:
recovering a crude organic light emitting material comprising the compound of Formula (1) from a deposition apparatus used in a process for depositing an organic emitting material to prepare an organic light emitting device;
removing impurities from the crude organic light emitting material;
recovering the organic light emitting material after the impurities are removed; and
purifying the recovered organic light emitting material to have a purity of 99.9% or higher.

\* \* \* \* \*